United States Patent
Chiang et al.

(10) Patent No.: US 8,551,000 B2
(45) Date of Patent: Oct. 8, 2013

(54) ULTRASOUND 3D IMAGING SYSTEM

(75) Inventors: Alice Chiang, Weston, MA (US);
Xingbai He, Andover, MA (US);
William Wong, Milton, MA (US); Noah Berger, Framingham, MA (US)

(73) Assignee: Teratech Corp., Burlington, MA (US)

( * ) Notice: Subject to any disclaimer, the term of this patent is extended or adjusted under 35 U.S.C. 154(b) by 535 days.

(21) Appl. No.: 12/286,555

(22) Filed: Sep. 30, 2008

(65) Prior Publication Data
US 2009/0156936 A1    Jun. 18, 2009

Related U.S. Application Data

(63) Continuation-in-part of application No. 11/474,098, filed on Jun. 23, 2006, now Pat. No. 7,874,991.

(51) Int. Cl.
*A61B 8/00* (2006.01)

(52) U.S. Cl.
USPC .......................................... 600/446; 600/437

(58) Field of Classification Search
USPC ................................... 600/437–469
See application file for complete search history.

(56) References Cited

U.S. PATENT DOCUMENTS

| | | |
|---|---|---|
| 5,235,982 A | 8/1993 | O'Donnell |
| 5,295,485 A | 3/1994 | Shinomura et al. |
| 5,435,313 A | 7/1995 | Noda et al. |
| 5,546,807 A | 8/1996 | Oxaal et al. |
| 5,590,658 A | 1/1997 | Chiang et al. |
| 5,622,177 A | 4/1997 | Breimesser et al. |
| 5,722,412 A * | 3/1998 | Pflugrath et al. .............. 600/459 |
| 5,817,024 A | 10/1998 | Ogle et al. |
| 5,832,923 A | 11/1998 | Engeler et al. |
| 5,893,363 A | 4/1999 | Little et al. |
| 5,911,692 A | 6/1999 | Hussain et al. |
| 5,938,611 A | 8/1999 | Muzilla et al. |
| 5,997,479 A | 12/1999 | Savord et al. |
| 6,106,471 A | 8/2000 | Wiesauer et al. |
| 6,106,472 A | 8/2000 | Chiang et al. |
| 6,111,816 A | 8/2000 | Chiang et al. |
| 6,224,556 B1 | 5/2001 | Schwartz et al. |
| 6,245,017 B1 | 6/2001 | Hashimoto et al. |
| 6,279,399 B1 | 8/2001 | Holm |
| 6,292,433 B1 | 9/2001 | Gilbert et al. |
| 6,375,617 B1 | 4/2002 | Fraser |
| 6,419,633 B1 | 7/2002 | Robinson et al. |
| 6,468,216 B1 | 10/2002 | Powers et al. |
| 6,482,160 B1 | 11/2002 | Stergiopoulos et al. |
| 6,491,634 B1 | 12/2002 | Leavitt et al. |
| 6,497,663 B2 | 12/2002 | Fraser et al. |
| 6,537,220 B1 | 3/2003 | Friemel et al. |
| 6,552,964 B2 * | 4/2003 | Chiang et al. ................. 367/138 |
| 6,558,325 B1 | 5/2003 | Pang et al. |

(Continued)

FOREIGN PATENT DOCUMENTS

| | | |
|---|---|---|
| EP | 1 491 913 (A2) | 12/2004 |
| JP | 2004008642 | 1/2004 |

(Continued)

*Primary Examiner* — Sanjay Cattungal
(74) *Attorney, Agent, or Firm* — McCarter & English, LLP

(57) ABSTRACT

The present invention relates to an ultrasound imaging system in which the scan head either includes a beamformer circuit that performs far field subarray beamforming or includes a sparse array selecting circuit that actuates selected elements. When used with second stage beamforming system, three dimensional ultrasound images can be generated.

18 Claims, 34 Drawing Sheets

(56) References Cited

U.S. PATENT DOCUMENTS

| | | | |
|---|---|---|---|
| 6,638,220 B2 | 10/2003 | Satoh | |
| 6,638,226 B2 | 10/2003 | He et al. | |
| 6,648,826 B2 | 11/2003 | Little et al. | |
| 6,671,227 B2 | 12/2003 | Gilbert et al. | |
| 6,679,847 B1 | 1/2004 | Robinson et al. | |
| 6,709,395 B2 | 3/2004 | Poland | |
| 6,716,174 B1 * | 4/2004 | Li | 600/447 |
| 6,721,235 B2 * | 4/2004 | Chiang et al. | 367/138 |
| 6,821,251 B2 | 11/2004 | Alexandru | |
| 6,836,159 B2 | 12/2004 | Wodnicki | |
| 6,865,140 B2 | 3/2005 | Thomenius et al. | |
| 6,869,401 B2 | 3/2005 | Gilbert et al. | |
| 6,875,178 B2 | 4/2005 | Phelps et al. | |
| 6,890,301 B2 | 5/2005 | Jago et al. | |
| 6,967,975 B2 | 11/2005 | Van Stalen et al. | |
| 6,974,417 B2 | 12/2005 | Lockwood | |
| 6,980,844 B2 | 12/2005 | Schoisswohl | |
| 7,044,912 B2 | 5/2006 | Babu et al. | |
| 7,079,132 B2 | 7/2006 | Sauer et al. | |
| 7,115,093 B2 | 10/2006 | Halmann et al. | |
| 7,131,947 B2 | 11/2006 | Demers | |
| 7,141,020 B2 | 11/2006 | Poland et al. | |
| 7,150,716 B2 | 12/2006 | Jones et al. | |
| 7,169,108 B2 | 1/2007 | Little et al. | |
| 7,217,243 B2 | 5/2007 | Takeuchi | |
| 7,227,813 B2 | 6/2007 | Miller | |
| 7,270,634 B2 | 9/2007 | Scampini et al. | |
| 7,285,094 B2 | 10/2007 | Nohara et al. | |
| 7,297,118 B2 | 11/2007 | Kristoffersen | |
| 7,302,092 B1 | 11/2007 | Fenster et al. | |
| 7,322,936 B2 | 1/2008 | Takeuchi | |
| 7,347,820 B2 | 3/2008 | Bonnefous | |
| 7,448,998 B2 | 11/2008 | Robinson | |
| 7,527,591 B2 | 5/2009 | Haugen et al. | |
| 7,527,592 B2 | 5/2009 | Haugen et al. | |
| 7,529,393 B2 | 5/2009 | Peszynski et al. | |
| 7,563,228 B2 | 7/2009 | Ma et al. | |
| 2002/0091317 A1 | 7/2002 | Chiao | |
| 2002/0120193 A1 | 8/2002 | Chiang et al. | |
| 2004/0267135 A1 | 12/2004 | Takeuchi | |
| 2005/0057284 A1 | 3/2005 | Wodnicki | |
| 2005/0090745 A1 * | 4/2005 | Steen | 600/447 |
| 2005/0110793 A1 * | 5/2005 | Steen | 345/536 |
| 2005/0113698 A1 | 5/2005 | Kristoffersen et al. | |
| 2005/0124884 A1 | 6/2005 | Bolorforosh et al. | |
| 2005/0243812 A1 * | 11/2005 | Phelps | 370/360 |
| 2005/0288588 A1 | 12/2005 | Weber et al. | |
| 2006/0058667 A1 | 3/2006 | Lemmerhirt et al. | |
| 2006/0064014 A1 | 3/2006 | Falco | |
| 2006/0074310 A1 | 4/2006 | Thiele | |
| 2006/0241468 A1 | 10/2006 | Lu et al. | |
| 2007/0088213 A1 | 4/2007 | Poland | |
| 2007/0232910 A1 | 10/2007 | Hwang et al. | |
| 2008/0009739 A1 * | 1/2008 | Chiang et al. | 600/459 |
| 2008/0027320 A1 | 1/2008 | Bolorforosh et al. | |
| 2008/0027323 A1 | 1/2008 | Freiburger | |
| 2008/0106976 A1 | 5/2008 | Davidsen et al. | |
| 2008/0242996 A1 | 10/2008 | Hall et al. | |
| 2008/0262357 A1 | 10/2008 | Wodnicki | |
| 2009/0003665 A1 | 1/2009 | Berg et al. | |
| 2009/0005684 A1 | 1/2009 | Kristoffersen et al. | |
| 2009/0030313 A1 * | 1/2009 | Prater et al. | 600/443 |
| 2009/0149756 A1 | 6/2009 | Soler et al. | |
| 2009/0203996 A1 | 8/2009 | Thiele et al. | |

FOREIGN PATENT DOCUMENTS

| | | |
|---|---|---|
| WO | WO 98/34294 (A2) | 8/1998 |
| WO | WO 98/34294 (A3) | 8/1998 |
| WO | WO 2006/038177 | 4/2006 |
| WO | WO 2006/038178 | 4/2006 |
| WO | WO 2006/038180 | 4/2006 |
| WO | WO 2007/029199 | 3/2007 |

* cited by examiner

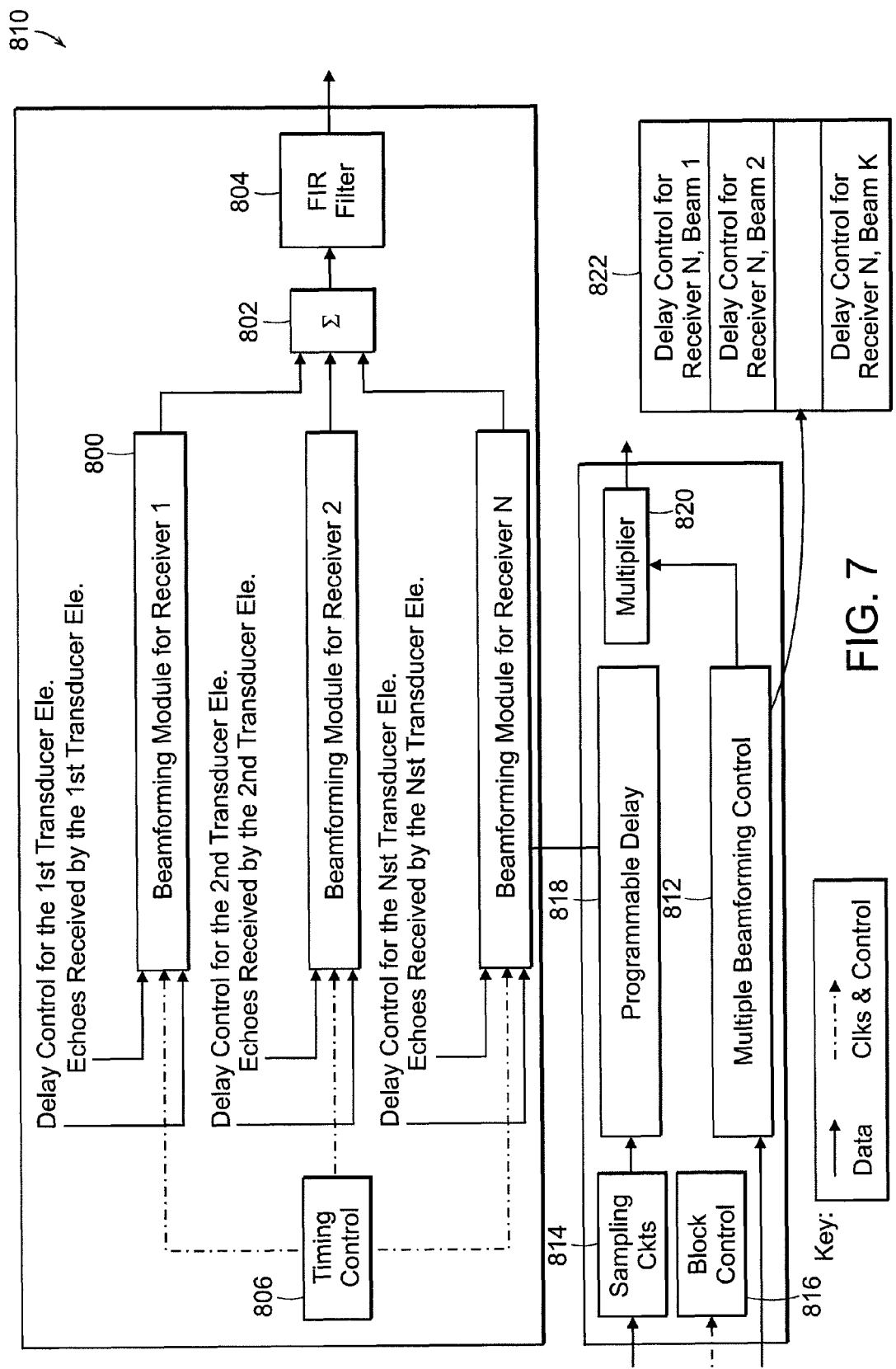

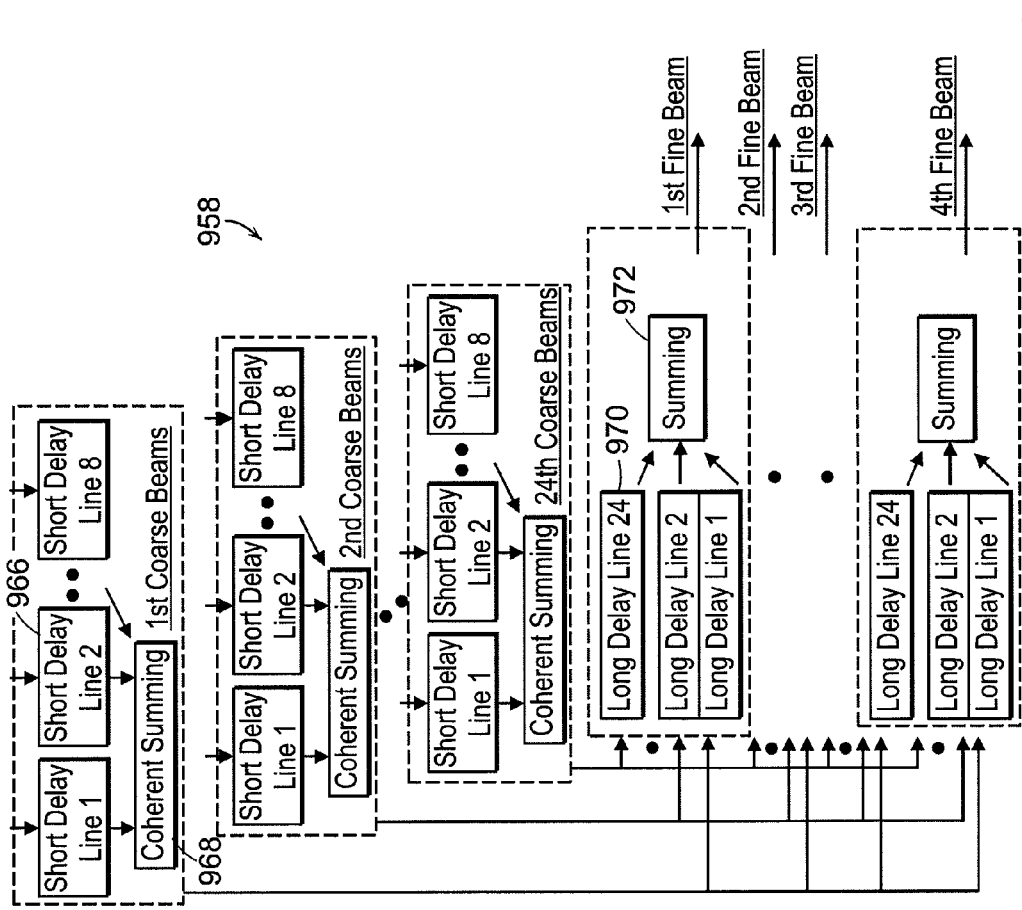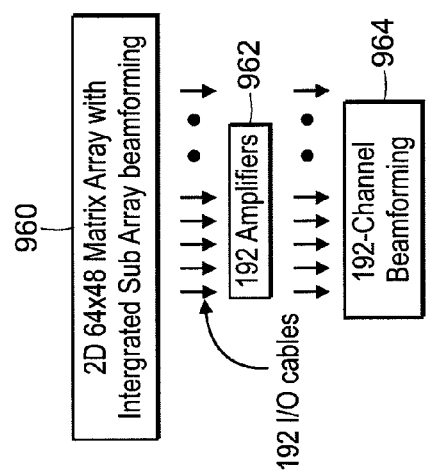
FIG. 22A

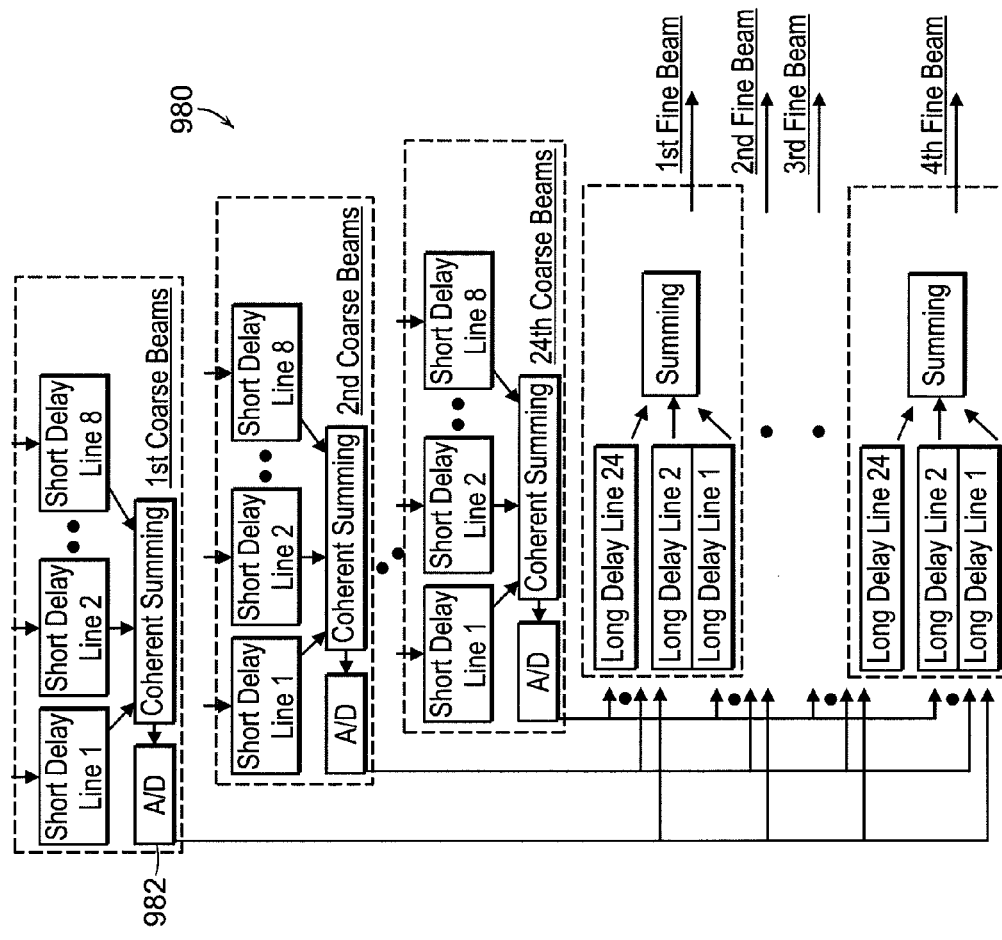
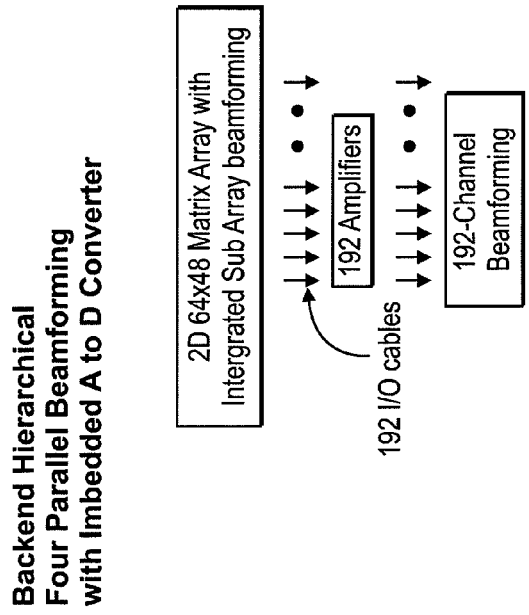
FIG. 22C
Backend Hierarchical Four Parallel Beamforming with Imbedded A to D Converter

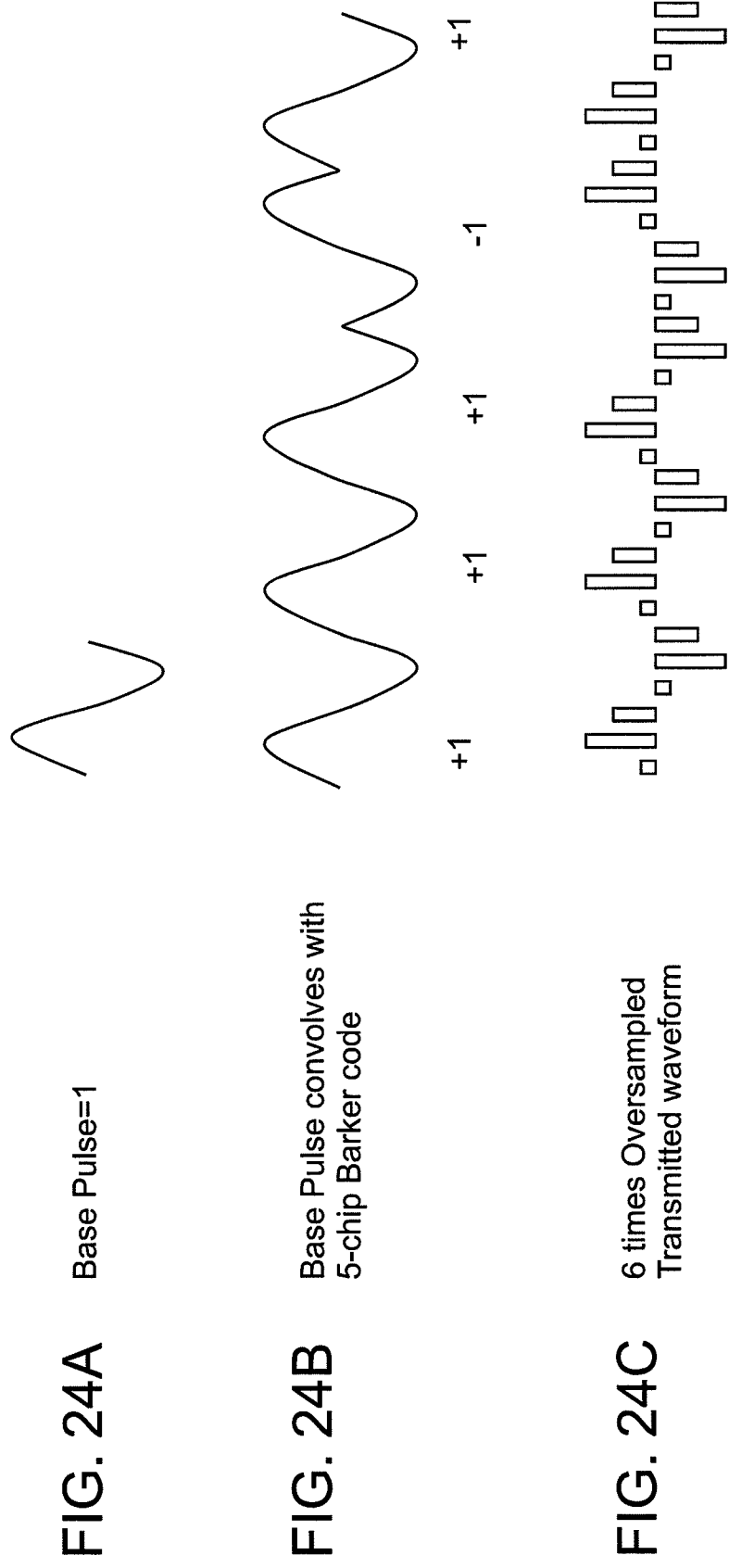

ULTRASOUND 3D IMAGING SYSTEM

CROSS REFERENCE TO RELATED APPLICATION

This application is a continuation-in-part of U.S. application Ser. No. 11/474,098, filed Jun. 23, 2006 and also of International Application No. PCT/US2007/014526 filed Jun. 22, 2007. The application also claims priority to U.S. Application No. 61/192,063 filed on Sep. 15, 2008 by Chiang et al., entitled: "Ultrasound 3D Imaging System." The entire contents of the above applications are incorporated herein by reference.

BACKGROUND OF THE INVENTION

Medical ultrasound imaging has become an industry standard for many medical imaging applications. Techniques have been developed to provide three dimensional (3D) images of internal organs and processes using a two dimensional (2D) transducer array. These systems require thousands of beamforming channels. The power required to operate such systems has resulted in the use of an analog phase shift technique with a digital delay beamformer that results in a compromise of image quality.

There is a continuing need for further improvements in ultrasound imaging technologies enabling improved real-time three dimensional imaging capability. In addition, this improved capability should support continuous real-time display for a fourth dimensional 4D function.

SUMMARY OF THE INVENTION

The present invention relates to a system for ultrasound medical imaging that provides three dimensional (3D) imaging using a two dimensional (2D) array of transducer elements in a probe housing. Embodiments of the invention provide systems and methods for medical imaging having high resolution and numerous imaging modalities.

In a preferred embodiment, the probe housing contains a first beamforming circuit that transmits beamformed data to a second housing having a second beamforming circuit. The first beamforming circuit provides a far-field subarray beamforming operation. The resulting beamformed data is transmitted from the scan head to a second housing having the second beamforming circuit that provides near-field beamsteering and beamfocusing.

A preferred embodiment provides a scan head that can be connected to a conventional ultrasound system in which the scan head provides the inputs to the conventional beamforming processing function. The scan head beamformer can utilize a low power charge domain processor having at least 32 beamforming channels.

A preferred embodiment of the invention employs a sparse array where only a fraction of the transducer elements need to be activated. By selecting the four corner elements of the array to provide proper mean lobe bandwidth, minimizing average sidelobe energy and clutter, eliminating periodicity and maximizing peak to side lobe ratio, quality images are produced. To steer the beams across the volume or region of interest, different transducer elements must be actuated in proper sequence to maintain the peak to sidelobe ratio. The system processor can be programmed to provide the desired sequence for transducer actuation to direct the beam at different angles. Alternatively, a discrete controller can be used to control sparse array actuation. A preferred embodiment provides a scan head with integrated switching circuits for sequentially selecting sparse array actuation elements for sequential multiple beamforming. The scan head can be connected to a conventional ultrasound system in which the scan head provides the inputs to the conventional beamforming processing functions. In another embodiment, the transmit array elements and receive array elements can be operated independently with the transmit elements comprising a sparse array and the receive elements being a near fully populated array. In a preferred embodiment, the multiplexer and beamformer circuits can be integrated into an interface system, or alternatively, into a host processing system, leaving a 2D transducer array mounted in the probe housing.

The present invention utilizes nondestructive sensing at each stage of the delay elements in the beamformer. So with a 65 stage delay line, for example, there are 64 usable outputs with one at each stage. The time resolution can be in the range of $1/8\lambda$ to $1/16\lambda$.

Using high voltage multiplexers in the probe and the nondestructive sensing allows for time multiplexed sequential beamforming. It is now possible to sequentially change tap selection of each delay line to form multiple beams.

In addition to the three dimensional (3D) display capability, a fourth dimension or time resolved image display can be used to record and display a sequence of images recorded at 10 frames per second or higher, for example. This enables viewing of rapidly changing features such as blood or fluid flow; heart wall movement etc. at video frames rates of 30 frames per second.

Another preferred embodiment of the invention utilizes a three stage beamformer system in which a first stage performs a first beamforming operation on data received from a transducer array, which generates first beamformed data that is followed by a second stage that performs a second beamforming operation to provide second stage beamformed data that is then delivered to a third beamforming stage that performs a third beamforming operation.

The stages can be performed using charge domain processors. Data can also be converted from analog to digital form before the first stage, or the second stage, at the third stage or thereafter. One stage can utilize parallel beamforming operations and a second stage provides serial beamforming.

BRIEF DESCRIPTION OF THE DRAWINGS

FIG. 7 illustrates an ultrasound system in accordance with the invention.

FIGS. 22A-22C illustrate embodiments of system processors in a four parallel beamforming system.

FIGS. 24A-24C illustrate a process for forming a transmission signal.

DETAILED DESCRIPTION OF THE INVENTION

The objective of the beamforming system is to focus signals received from an image point onto a transducer array. By inserting proper delays in a beamformer to wavefronts that are propagating in a particular direction, signals arriving from the direction of interest are added coherently, while those from other directions do not add coherently or cancel. For real-time three-dimensional applications, separate electronic circuitry is necessary for each transducer element. Using conventional implementations, the resulting electronics rapidly become both bulky and costly as the number of elements increases. Traditionally, the cost, size, complexity and power requirements of a high-resolution beamformer have been avoided by "work-around" system approaches. For real-time three-dimensional high-resolution ultrasound imaging applications, an electronically steerable two-dimensional beamforming processor based on a delay-and-sum computing algorithm is chosen.

Figure 1:
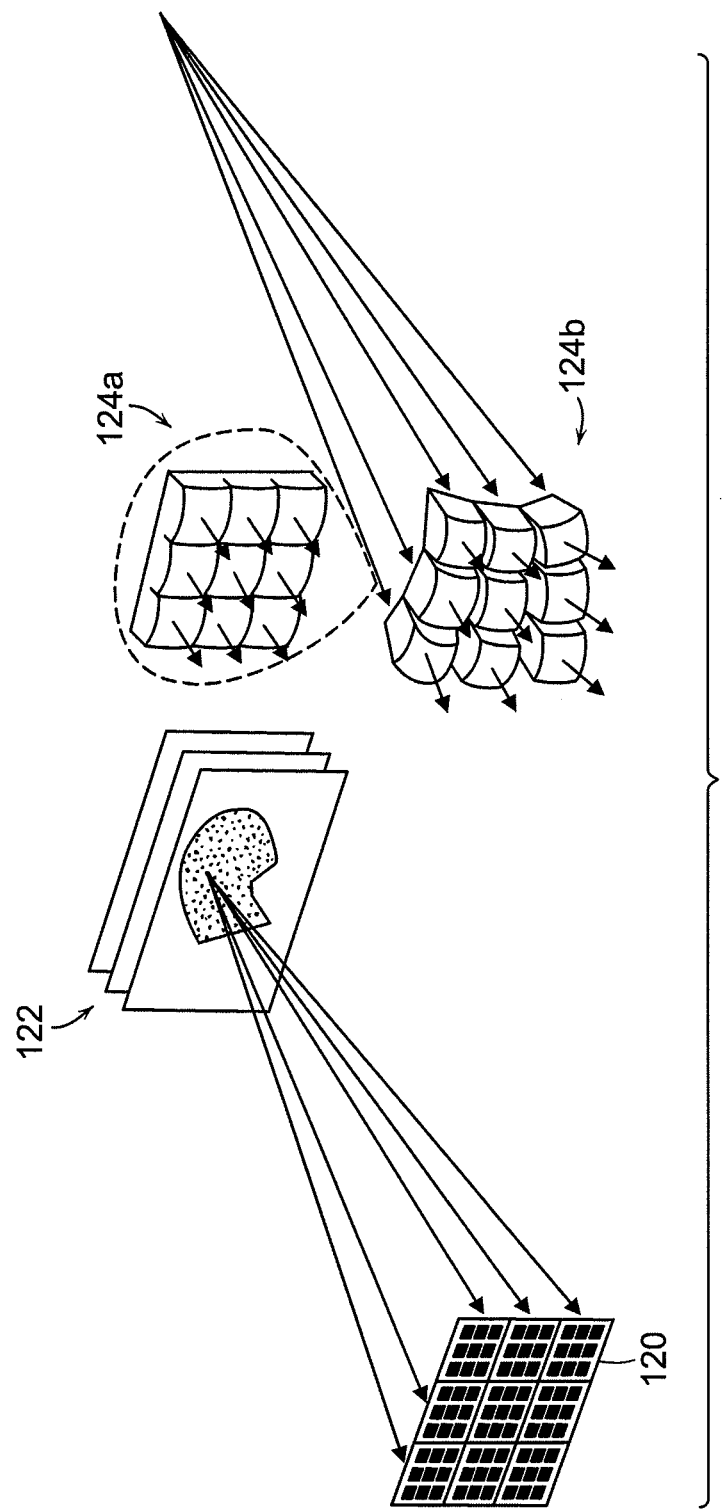
FIG. 1 illustrates the use of a two dimensional tiled array for ultrasound imaging in accordance with the invention.

The concept of an electronically-adjustable acoustic conformal lens is to divide the surface of a 2D transducer array into plane "tiles" of relatively small subarrays. As described in U.S. Pat. No. 6,292,433 the entire contents of which incorporated herein by reference, and illustrated in FIG. 1 the tiles/subarrays 120 are made small enough so that when an object is placed within the field-of-view of the imaging system, the incident radiation 122 from the object toward each "tile" can be treated using a far-field approximation. Additional delay elements are incorporated as second-stage processing to allow all subarrays to be coherently summed (i.e., global near-field beamforming can be achieved by simply delaying and then summing the outputs from all subarrays.) The delay-and-sum beamformer allows each subarray to "look" for signals radiating from a particular direction. By adjusting the delays associated with each element of the array, the array's look direction can be electronically steered toward the source of radiation. Thus instead of looking in one direction as seen at 124a, the direction of tiles 120 can be steered in different direction 124b. The delay line requirement for each element in the sub-array can be less than a hundred stages. Only long delays for global summing are needed for the final near field focusing.

Figure 2:
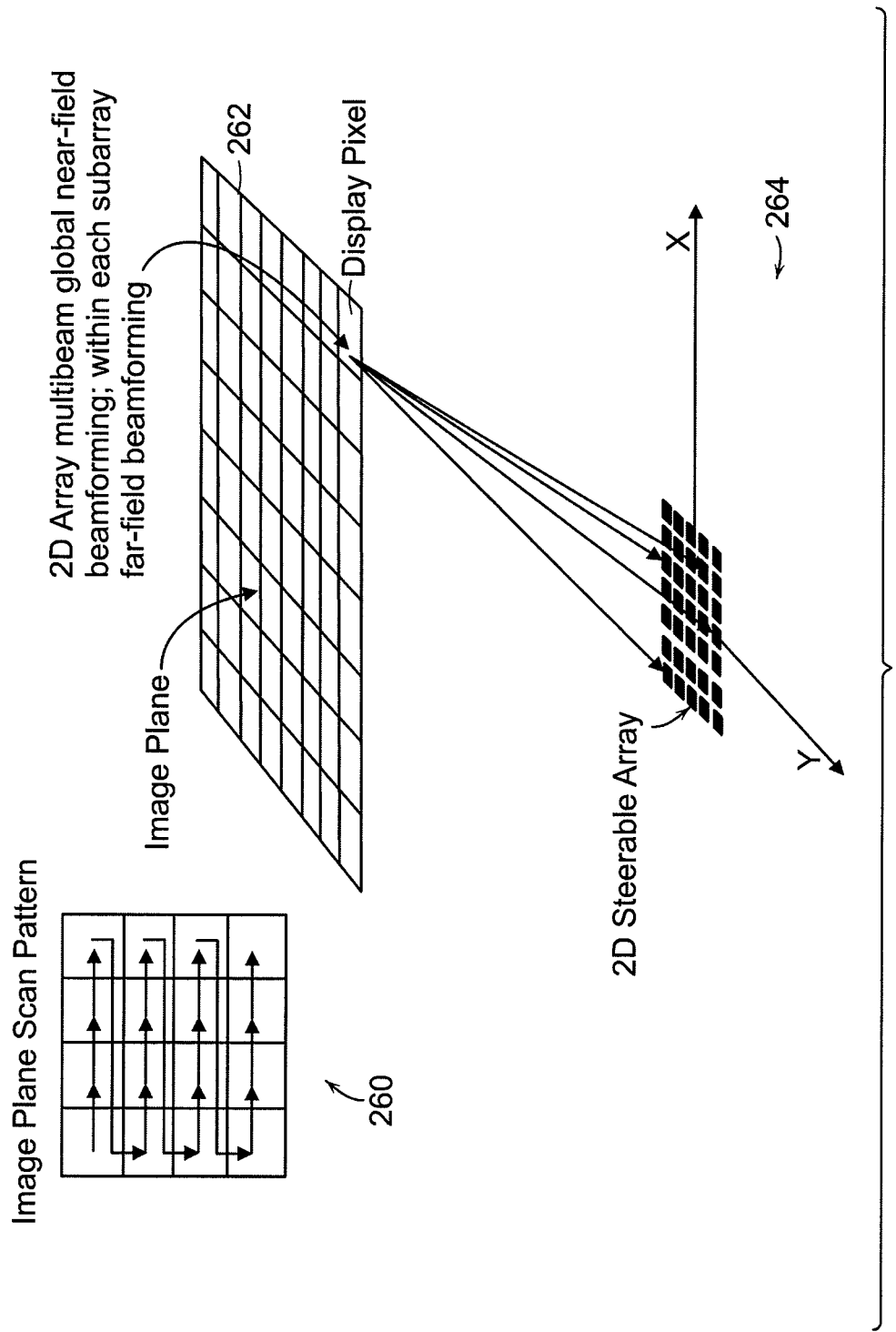
FIG. 2 illustrates a steerable two dimensional array in accordance with the invention.

To scan an image plane using a steerable beamformer system a process such as that shown in FIG. 2 can be used. A raster scan 260 can be used to scan an image plane 262 using a 2D steerable transducer array 264.

Figure 3A:
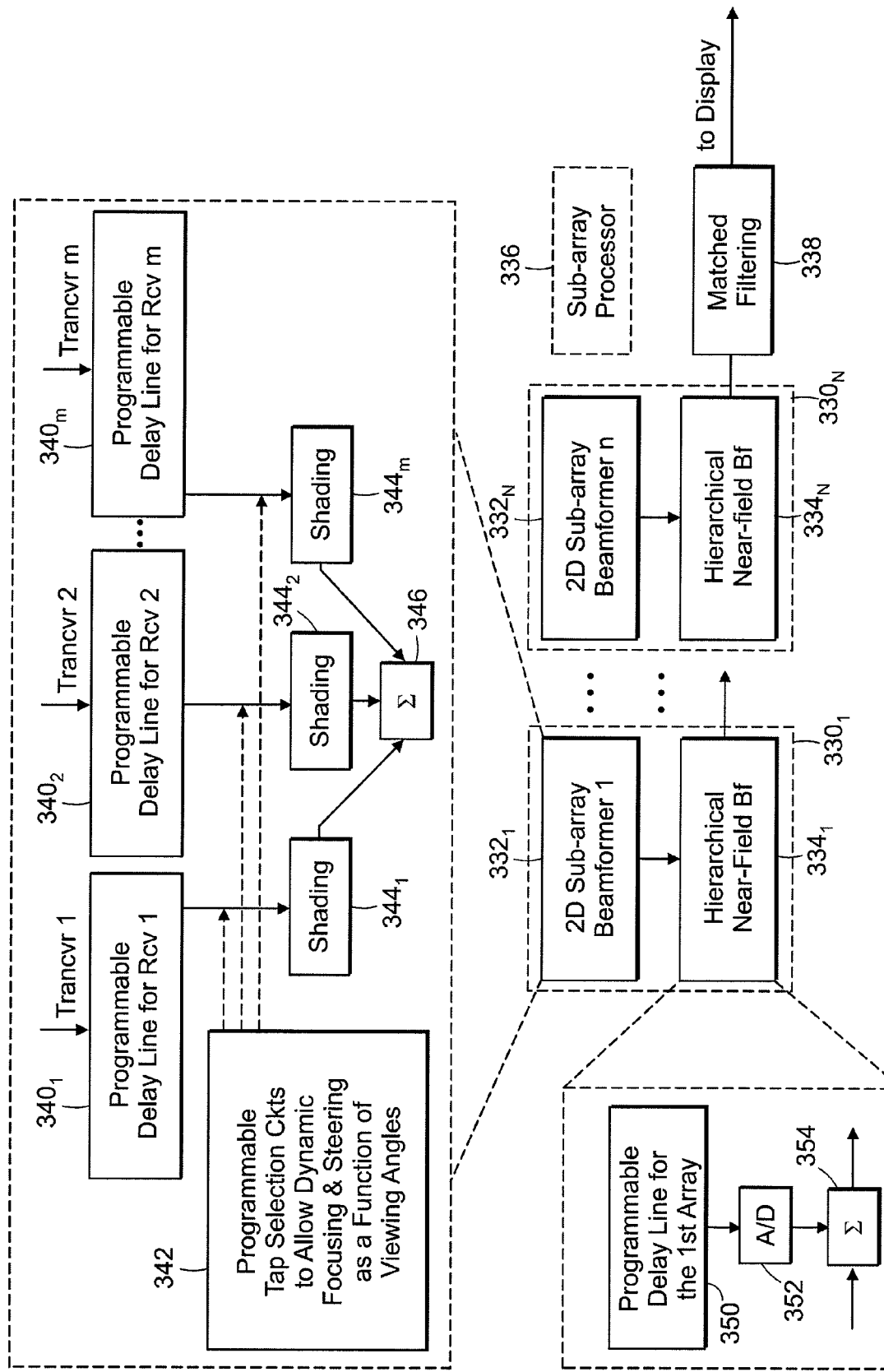
FIG. 3A illustrates the use of a first beamformer device for far field beamsteering and focusing and a second time delay beamformer for near field beamforming.
Figure 3B:
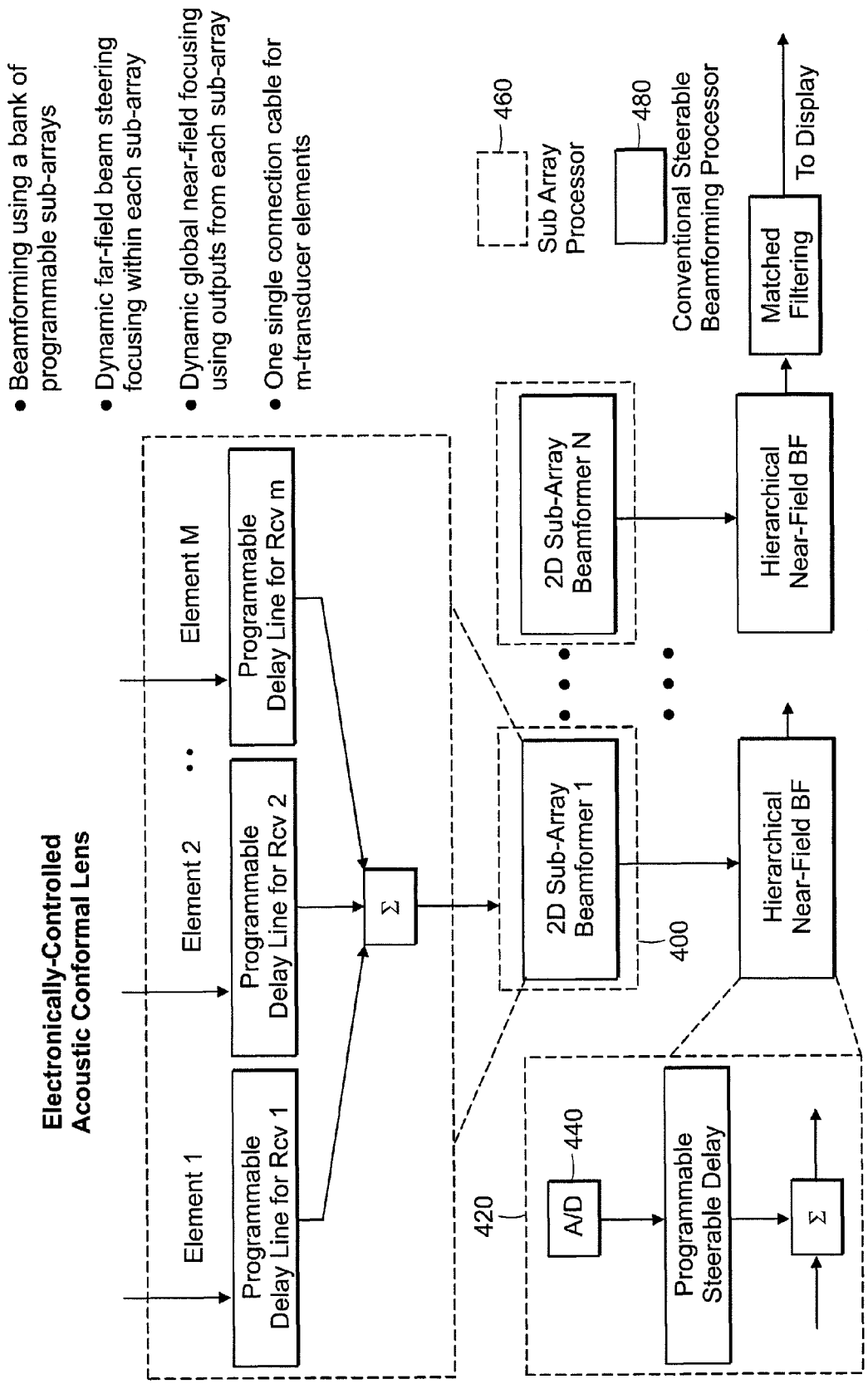
FIG. 3B illustrates a first analog subarray beamformer forwarding data to a digital beamformer near field beamformer.

A detailed diagram of an electronically-controlled beamforming system in accordance with the invention is shown in FIG. 3A. This system consists of a bank of parallel time-delay beamforming processors 330, -330N. Each processor 330 consists of two components: a 2D sub-array beamformer 332 for far-field beamsteering/focusing and an additional time delay processor 334 to allow hierarchical near-field beamforming of outputs from each corresponding subarray. The sub-arrays 332 include m-programmable delay lines 340 with tap selectors 342, multiplexers 344 and summed 346 output. As can be seen in FIG. 3A, for a system with n-sub-arrays, n-parallel programmable $2^{nd}$-stage near field time delays are needed for individual delay adjustment which are converted with A/D converter 352 to allow all n-parallel outputs be summed 354 coherently, in turn, this summed output is filtered 338 and provides the 3D images of the targeted object. A processor 336 controls sub-array operation. Use of the scan head with a second stage digital beamformer is shown in FIG. 3B. In this embodiment, a plurality of N sub-array beamformers 400 each receive signals from m transducer elements that have separate delay lines whose outputs are summed and provided to near-field beamformers 420 so that this beamformer can be a conventional system with conventional processor 480. A separate sub-array processor 460 controls beamformers 400.

Without using this hierarchical subarray far-field and then near-field beamforming approach, for an 80×80 element 2D array, a cable consisting of six thousand and four hundred wires is needed to connect the transducer array to a conventional beamforming system. As shown in FIG. 3A, the number of inputs to each subarray processor equals the total number of delay elements in the subarray, each sub-array only has a single output. The number of inputs to the subarray bank equals the number of 2D array elements, and the number of outputs from the subarray bank equals to the total transducer array element number divided by the subarray element number, i.e., the number of outputs from the subarray bank reference to the number of inputs is reduced by a factor equal to the size of the subarray. For example, if one selects to use a 5×5 subarray to implement this hierarchical beamforming concept, after the first stage subarray beamforming, the total number of wires needed to connect to the $2^{nd}$ stage near-field beamforming is reduced by a factor of 25. More specifically, as mentioned above, without using this 2D subarray beamforming, 6400 wires are needed to connect an 80×80 element 2D transducer array to a conventional back-end beamforming system. Using a 5×5 subarray processing bank first, the number of wires required to connect to the backend beamforming system is reduced to 256. Based on the current invention, a bank of 256 5×5 element subarrays Beamformer can be integrated with a 80×80 element 2D array in the scan head, so a cable consisting of 256 wires is adequate to connect the integrated scan head with the back-end near-field beamforming system. It is important to note that 5×5 subarray far-field beamforming processors can be easily integrated in a small size Si integration circuit, eight of such 5×5 subarray beamforming can be integrated on one chip. Only 32 chips integrated into the scan head, it can reduce the cable size from 6,400 wires down to 256 wires.

Figure 4:
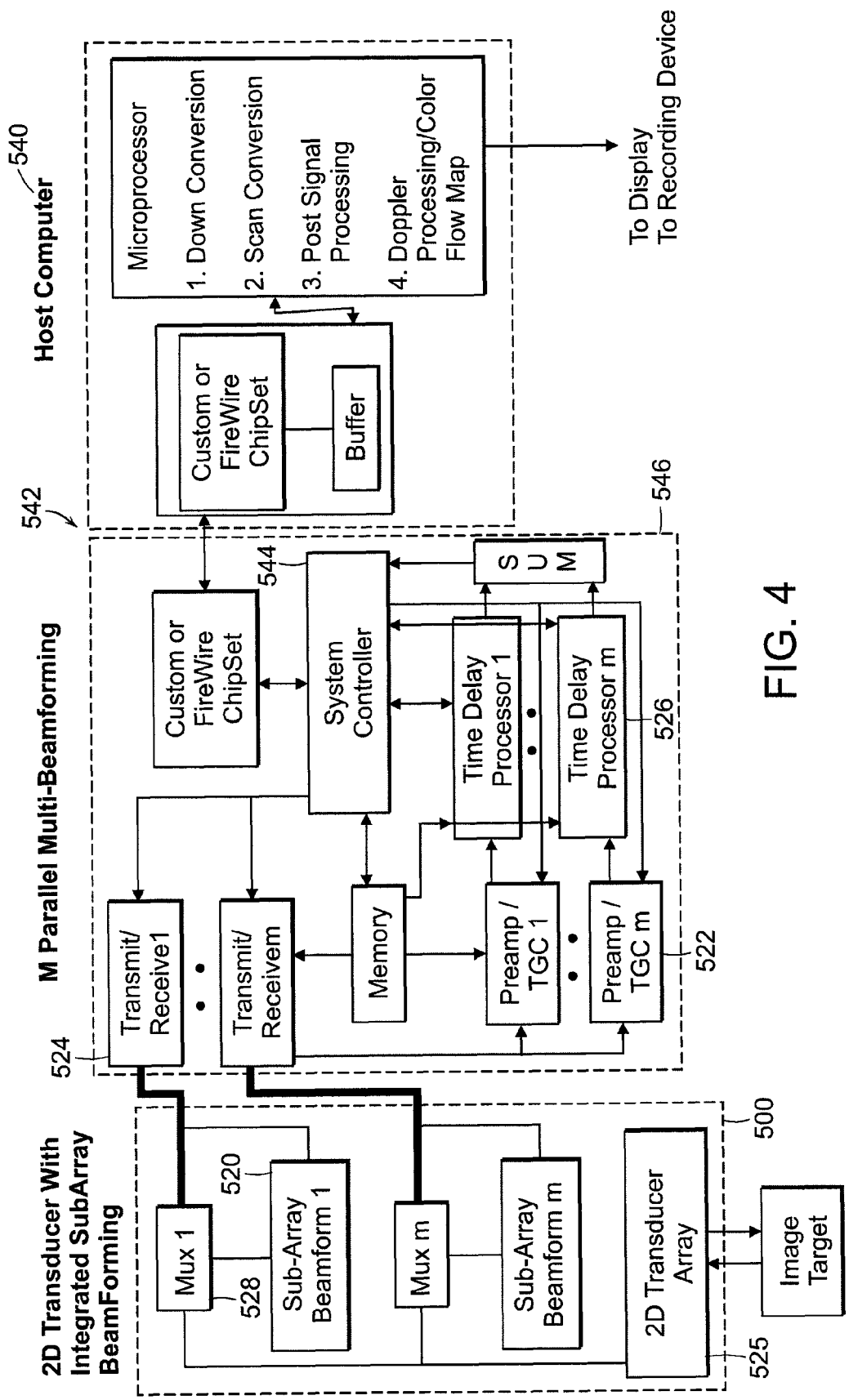
FIG. 4 illustrates a preferred embodiment of a three dimensional imaging system in accordance with the integrated Subarray scan head invention.
Figure 5:
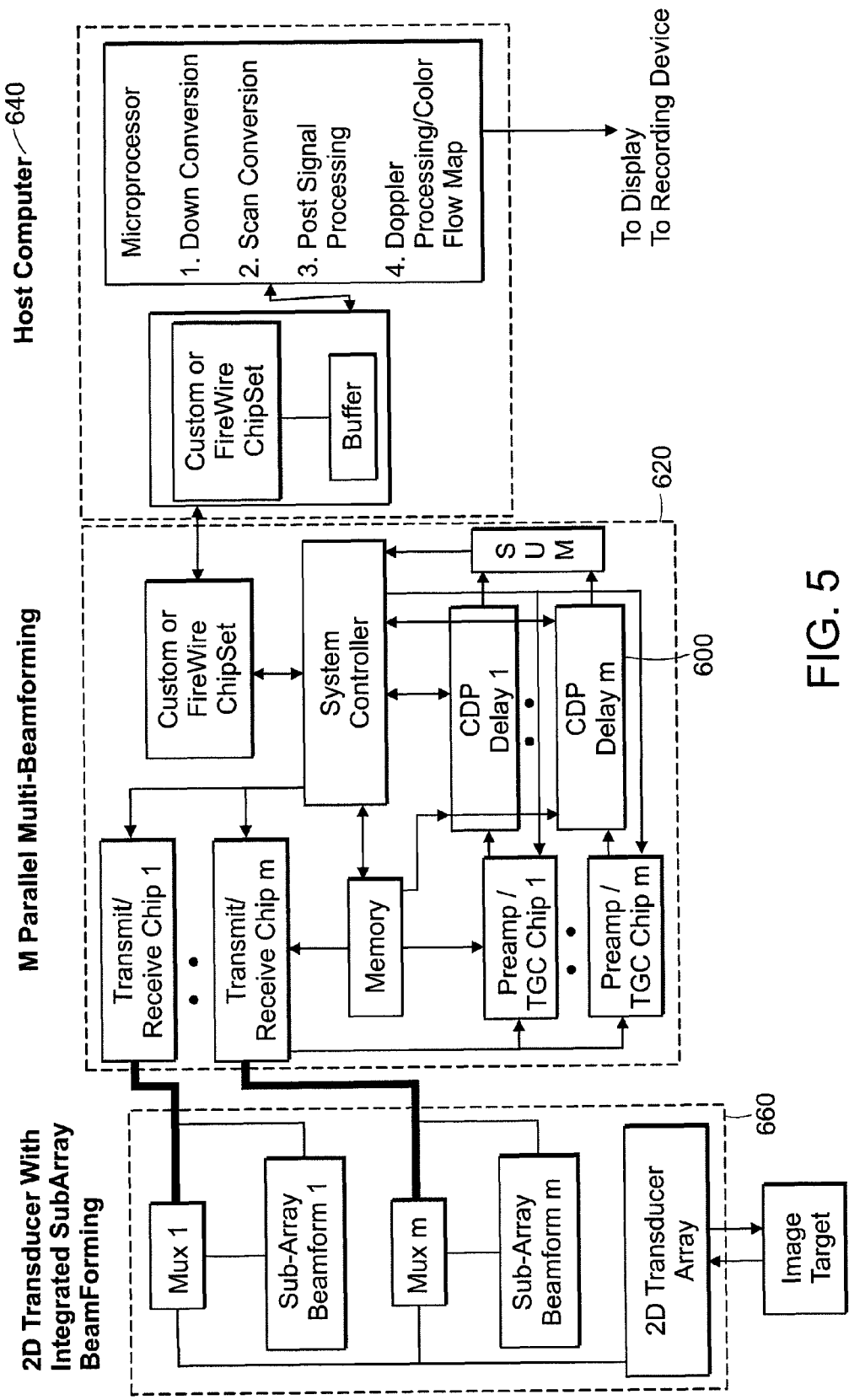
FIG. 5 illustrates a preferred embodiment of the integrated Subarray scan head invention using a charge domain processor for the $2^{nd}$ time delay beamforming.
Figure 6A:
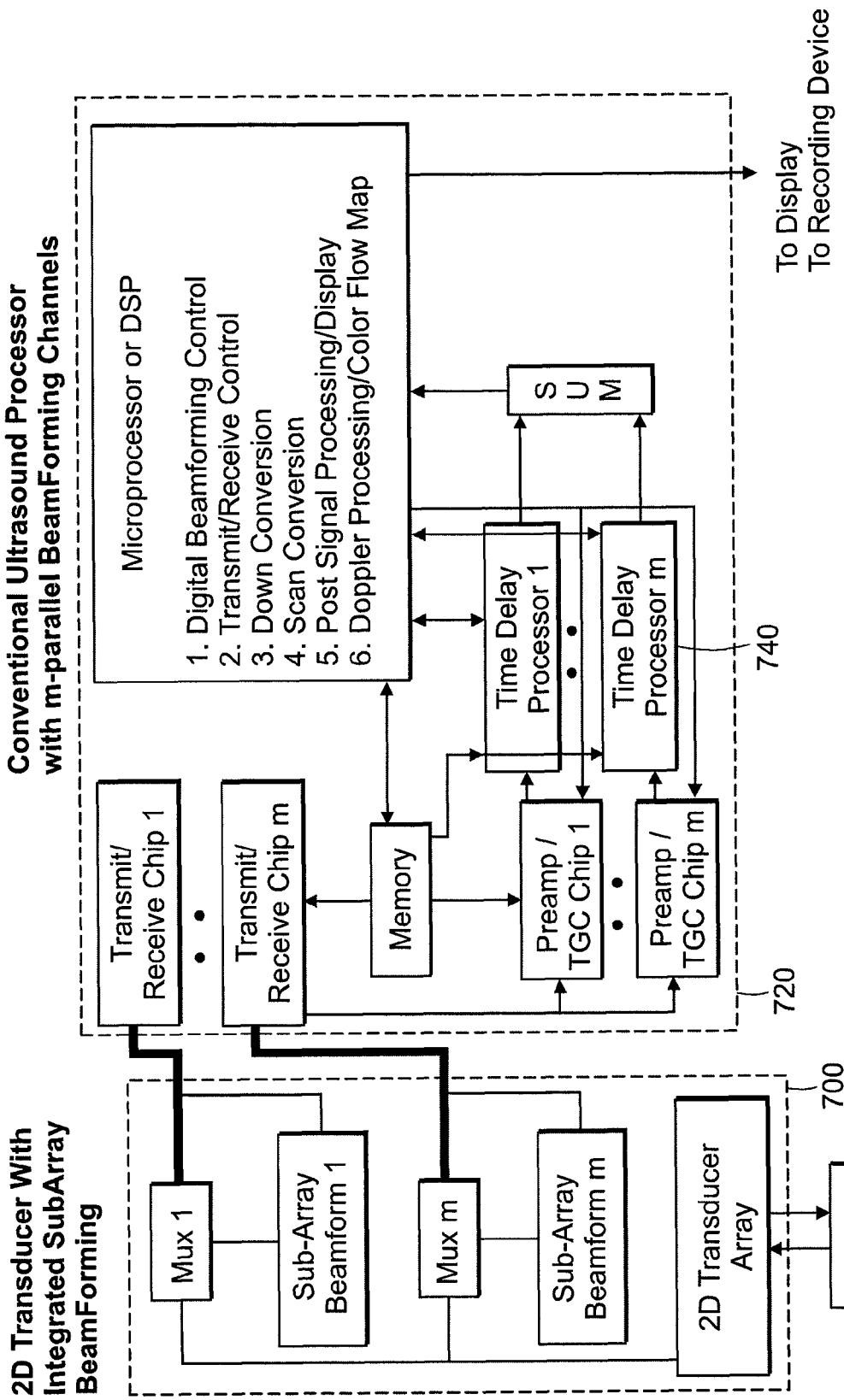
FIG. 6A illustrates the use of the integrated subarray scan head probe of the present invention with a second stage beamforming ultrasound processor.
Figure 6B:
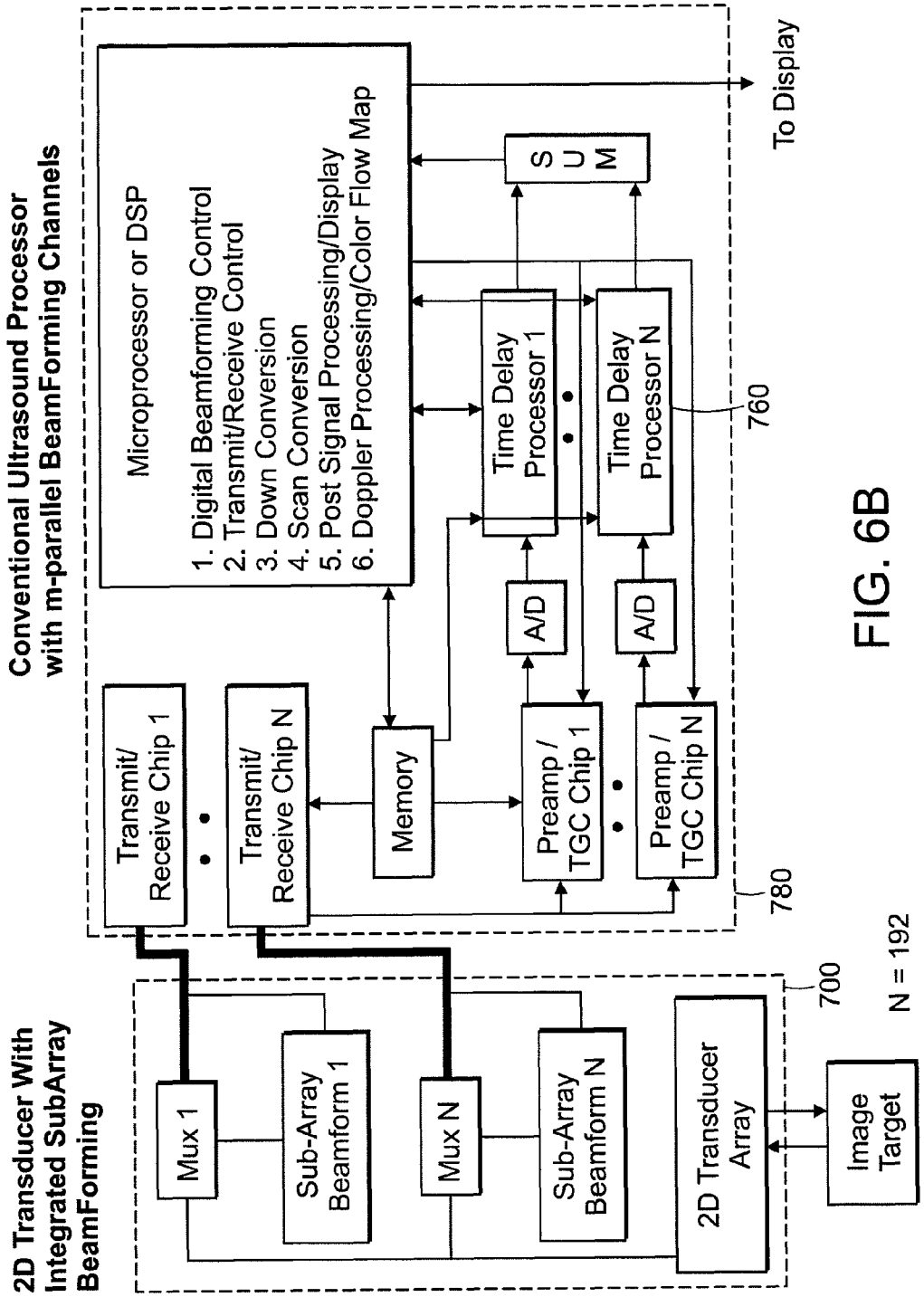
FIG. 6B illustrates use of the integrated Subarray scan head with a digital beamforming processor.

A preferred embodiment of the invention for a 2D array beamforming, each minimizing noise and cable loss with improved S/N performance, are described in FIGS. 4, 5 and 6. In all three implementations, the bank of m parallel subarray beamforming processors 520 and multiplexers 528 are integrated with the 2D transducer array 525 to create a compact, low-noise, scan head 500. FIG. 4 depicts a system that the compact scan head is connected to a dedicated processing module, in which the m-parallel preamp/TGCs 522 transmit/received chips 524 and the $2^{nd}$ stage time delay processing units 526 are housed. This dedicated processing module communicates with a host computer 540 via FireWire IEEE 1394 or USB or PCI bus 542. Control and synchronization is performed by the system controller 544 located in the processing module or housing 546. FIG. 5 depicts the same architecture as stated in FIG. 4, except, inside the dedicated processing module, the $2^{nd}$ stage time delay processing units are specifically implemented by using charge-domain programmable (CDP) time-delay lines 600 in housing 620 that is connected to handheld probe 660 and computer housing 648. FIG. 6B depicts a system that the compact sparse array scan head 700 is connected to a conventional, commercially available time-domain digital ultrasound imaging system 700 with n-parallel beamforming channels 760. It is easy to see that in FIG. 6A, the time-delay processor 720 can also be implemented by using CDP time-delay lines 740. In these embodiments the near-field beamforming is housed 720, 780 in the same housing with other image processing functions. These systems are described in International Application No. PCT/US2007/014526 filed Jun. 22, 2007, designating the U.S. and U.S. application Ser. No. 11/474,098 filed Jun. 23, 2006, both applications being incorporated herein by reference in their entirety.

By systematically varying beamformer delays and shading along a viewing angle of a 2D transducer array, returned echoes along the line of sight representing the 3D radiation sources can be used to create the scanned image at the scanned angle. The system can provide continuous real-time large area scanned images throughout a large field of view at 20 frames/s or more. At this frame rate, the system can be used to display continuous 3D images vs. time, thus providing 4D information of the scanned object. As shown in FIG. 7 a CDP beamforming chip 810, a time multiplexed computing structure can be used to generate multiple beams, i.e., for each transmit pulse, the bank of 2D subarray beamformers 818 and its corresponding $2^{nd}$ stage near-field time-delay line are capable of providing multiple beams sequentially. The computing circuits sequentially generate the delays required for forming K beams. The device operates as follows. Once a set of sampled returned-echoes are loaded in the delay lines with sampling circuits 814, at time $t_1$, the delays required for forming beam 1 are computed 812 within each module 822 and applied in parallel to all delay lines. The sampled return-echoes with proper delays are coherently summed 802 and filtered 804 to form the first beam. At time $t_2$, the delays required for forming beam 2 are computed within each module and applied in parallel to all delay lines. The sampled return-echoes with proper delays are coherently summed to form the second beam. The procedure repeats until the Kth beam is coherently formed.

For example, if a computing circuit with 16-serial addressable outputs is built in with the CDP subarray and the $2^{nd}$ stage time delay lines, for each transmit pulse, 16 beams or scan lines each along a different scan angle can be created. For 256-pulses with a down-range depth of 15 cm, the system can generate a 4096-beams with a 64×64 pixel resolution at a frame rate of 20 frames/s. The system is fully programmable; the beamforming electronics can be adjusted to zoom-in to a smaller field-of-view for high-resolution or higher frame rate images. For example, using 192-transmit pulses with the same down-range depth of 15 cm, the system can generate a 3072-beams with a 64×48 pixel resolution at a 30 frame/s frame rate.

The array described addresses ultrasound imaging applications using a two-dimensional 2 cm×2 cm array at a frequency of 3 MHZ. The need for resolution on the order of less than half the wavelength dictates as large an aperture as possible that can be housed within a compact package. To interrogate a 90 degree scanning volume and also minimize the impact of grating lobes, an element pitch or separation of less than 0.25 mm is desirable, leading to a 80×80 element array. Using the subarray processing technique described above, a scan head with integrated subarray beamforming circuits followed by a $2^{nd}$ stage near-field beamsteering/beamfocusing system provides a practical implementation. However, the implementation still requires at least 32 subarray chips to be integrated on a scan head. An alternative pseudo random array design approach can be used to achieve this resolution with a much less amount of processing components in the scanned head.

To make a sparse array practical, the combination of low insertion loss and wide bandwidth performance is important for realizing acceptable imaging performance with low illumination levels. Quarter-wave matching layers with low acoustic impedance, but physically solid backing results in a robust array that loses only 3-4 dB in the conversion of received signal energy to electrical energy. Array bandwidths of 75% or more are typical of this design and construction process. Also, the transducer array employs element positioning and an interconnect system suitable for the beamformer circuitry. The electronics are mounted on printed-circuit boards that are attached to the transducer elements via flexible cables. In practice, a majority of the array elements are connected to outputs using the flexible cables. However, only a small fraction of the total number of elements are wired to the circuit boards. Nevertheless, the large number of array element connections are sufficient to insure a unique pattern of active-element locations in the final array.

As an example of a sparse array, assuming a 2×2 cm array with 256 active elements, the resulting filling factor is 4%. The output signal to noise ratio of the array is proportional to the number of active elements, so this filling factor corresponds to a loss in sensitivity of −13 dB when compared to a filled array of the same dimensions. To compensate for this loss, a transmitted signal of wider bandwidth is chosen to increase array sensitivity. In the approach presented here, the sensitivity is increased on the order of 10 dB. Further details regarding sparse array devices can be found in U.S. Pat. No. 6,721,235, the contents of which is incorporated herein by reference.

Figure 8A:
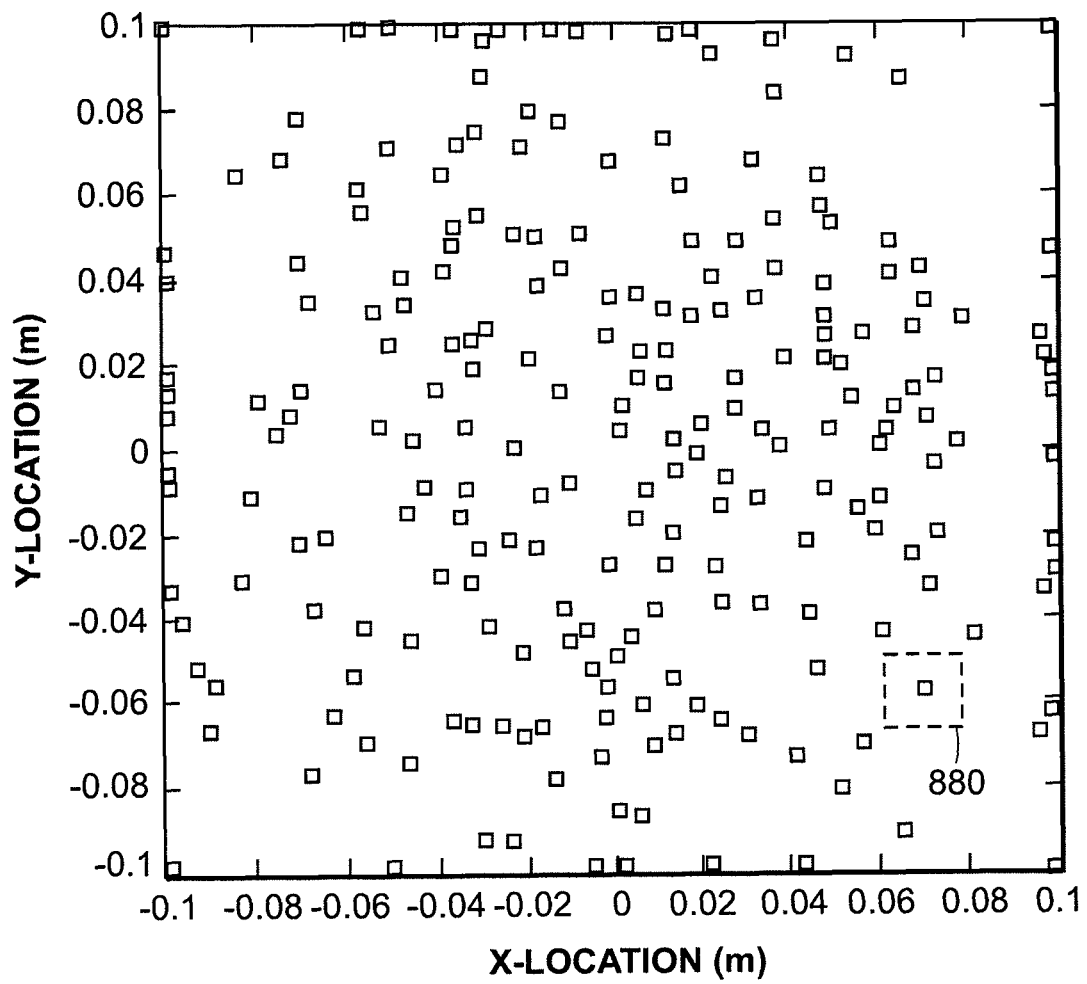
FIG. 8A illustrates a sparse array used in accordance with the invention.

Positioning the elements of the array follows the approach in which care must be taken to eliminate any periodicity that would produce grating lobes that compete with the main lobe. Pseudorandom or random arrays can be used (FIG. 8A). The geometry of activated element placement has been developed to maximize the efficiency of the beamformers while minimizing grating and side lobe clutter. Switching between a plurality of different array patterns is used to provide the most efficient beam pattern at different beam angles relative to the region or volume of interest being scanned. Thus, a first pattern can utilize that illustrated in FIG. 8A, which is than switched to a second pattern for a different scan angle. This can involve selecting a transducer element within a neighborhood 880 surrounding a given element to scan at a second angle.

The primary goal of the optimization method is to minimize the average side lobe energy. Specifically, this is done by interactively evaluating the optimization criterion:

$$J = \frac{1}{2\mu_{max}^2} \int \int_S W(u_x, u_y) B(u_x, u_y) du_x du_y, \qquad (1)$$

where the weighting function, $W(u_x, u_y)$, applies more weight to regions in the array response that require side lobe reduction. The optimization method begins with no weighting (i.e., $W(u_x, u_y)=1$) and proceeds by choosing successively better weighting functions that satisfy the optimization criterion. Since the side lobes that require the greatest reduction are related to the previously computed beampattern, $B(u_x, u_y)$, the weighting is chosen such that $W(u_x, u_y)=B(u_x, u_y)$. This is done in an interactive manner until convergence.

Basically, a random array is capable of producing an imaging point spread function that has a main lobe to average side lobe ratio of N, where N is the total number of active elements in the array. For the 256-element sparse array example, the resulting ratio is −13 dB. Using a wide bandwidth approach improves this ratio by 10 dB. Based on the preceding optimization criterion, a pseudorandom placement of the array elements was generated (FIG. 8A).

Figure 8B:
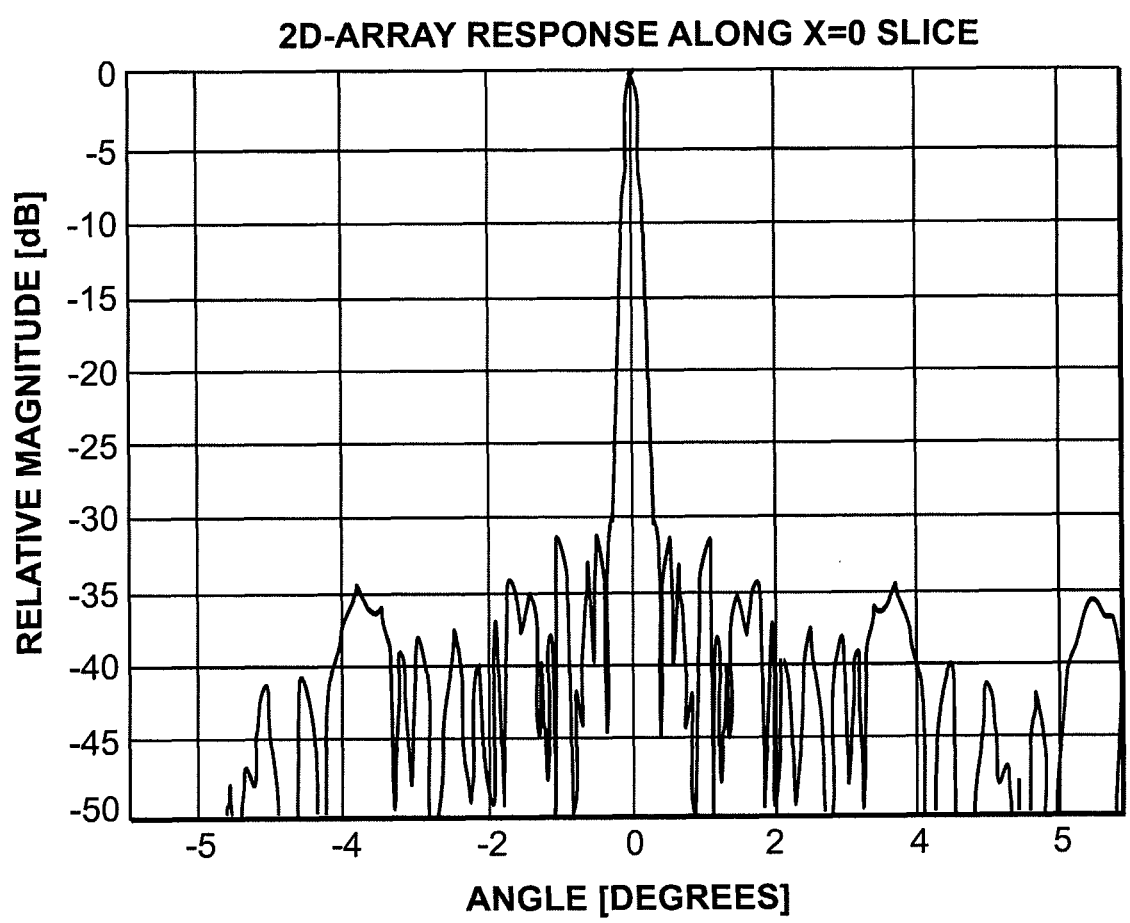
FIG. 8B graphically illustrates the sparse array performance.

FIG. 8B is a plot of the array performance, sensitivity versus cross range, for a 256-element sparsely-sampled array at 3 MHZ. The peak to maximum side lobe level is approximately 30 dB. To improve this performance, the system is configured to achieve the maximum main lobe to clutter level ratio possible, which has been independently verified.

Figure 9A:
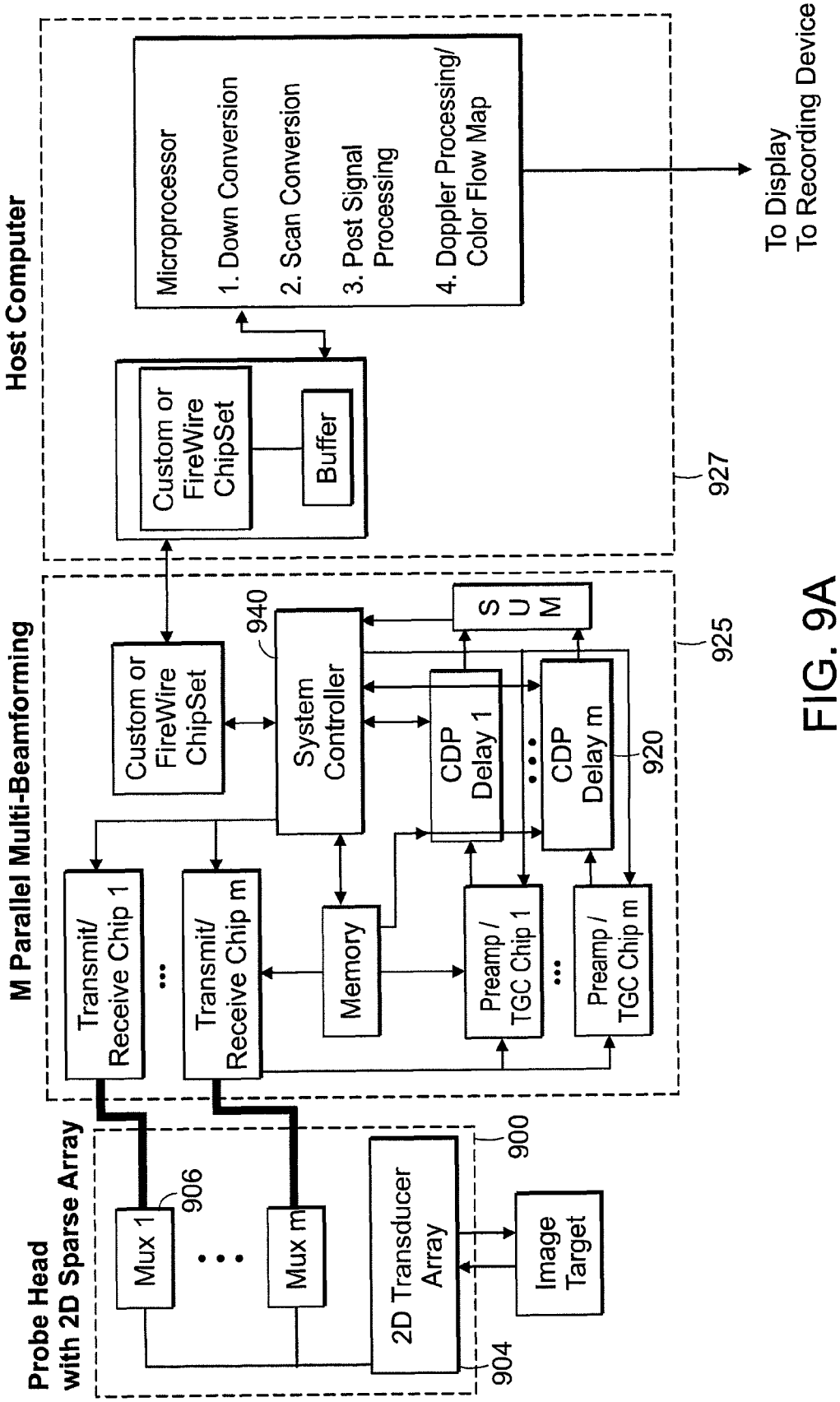
FIG. 9A illustrates the use of the integrated sparse array scan head probe of the present invention connected to a host system with charge-domain beamforming processing.
Figure 9B:
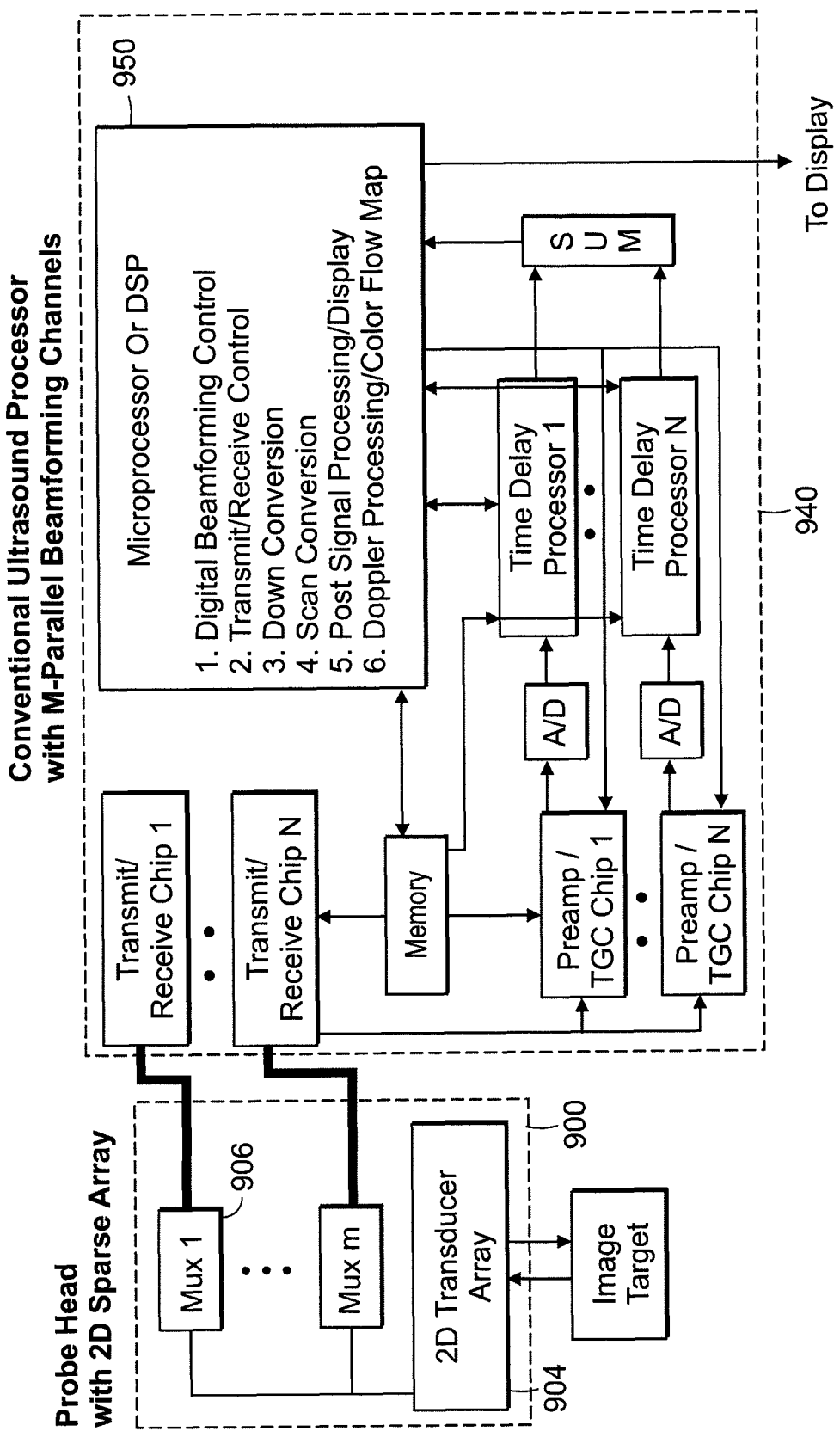
FIG. 9B illustrates the use of the integrated sparse array scan head probe of the present invention connected to a conventional digital ultrasound system with m-parallel beamforming components.

FIG. 9B depicts a system that the sparse array scan head 900 is connected to a conventional, commercially available time-domain digital ultrasound imaging system 940 with m-parallel beamforming channels. It is easy to see that in FIG. 9A, the time-delay processor can also be implemented by using CDP time-delay lines 920 in housing 925 that is connected to a separate computer 927. An array of m multiplexers 906 is used to switch between a sequence of scan patterns executed using a software program and system controller 940 or processor 950. The sequence of sparse array patterns is thus selected to scan at different scan angles of an object being imaged to provide 3D ultrasound imaging thereof.

A commercially available window-based 3D visualization software can be used to visualizing, manipulating, and analyzing the 3D multiple-beams volume image data generated by the electronically-adjustable acoustic conformal lens system. Traditionally, a clinician with 2D ultrasound images for diagnosis would look at the 2D scanned images slice by slice and mentally reconstruct the information into a 3D representation to judge the anatomy of the patient. This procedure requires the clinician to have well-founded experience as well as a highly sophisticated understanding of human anatomy. To create a "complete" image to the 3D structures, the clinician has to take all available slices into account. Looking at hundreds of slices is too time-consuming, even for a single patient. 3D visualization based on 3D volume data can help overcome this problem by providing the clinician with a 3D representation of the patient's anatomy reconstructed from the set of multiple-scanned beamforming data.

A commercially available software tool such as KB-Vol3D of KB-VIS technologies, Chennai, India, provides display or viewing 3D features such as:

Fast Volume-Rendering

Shaded Surface Display

Shaded-Surface module allows easy visualization of surfaces in the volume. Surfaces may be created by intensity-based thresholding. Alternatively, the Seeding option allows selection of specific connected structures of interest.

MIP (Maximum Intensity Projection) with Radials

MPR (Multiple-Plane-Reformating) with Oblique & Double-Oblique and 3D correlation MRP Slabs & Multi-Cuts Curved MPR Color & Opacity Presets with Editor Region-Growing and Volume Measurements Cutaway Viewing with Slab-Volume and Interactive Real-time VOI Volume-interiors are easily visualized using the "Cutaway-Viewing" tool. A Cut-Plane is used to slice through the volume, revealing the interior regions. The cut-plane is easily positioned and oriented using the mouse.

The VOI (Volume-of-Interest) tool allows interactive, real-time Volume-of-Interest display. The user can isolate and view sub-volumes of interest very easily and in real-time, using easy click-and-drag mouse operation.

Image Save in Multiple Formats

Images displayed by KB-Vol3D can be captured to various image formats (including DICOM, JPEG, and BMP etc.)

Movie Capture in AVI Format

Visualization operations can also be captured to an AVI movie .le and played on Windows Media Player, QuickTime, and Real Player etc.

Figure 10:
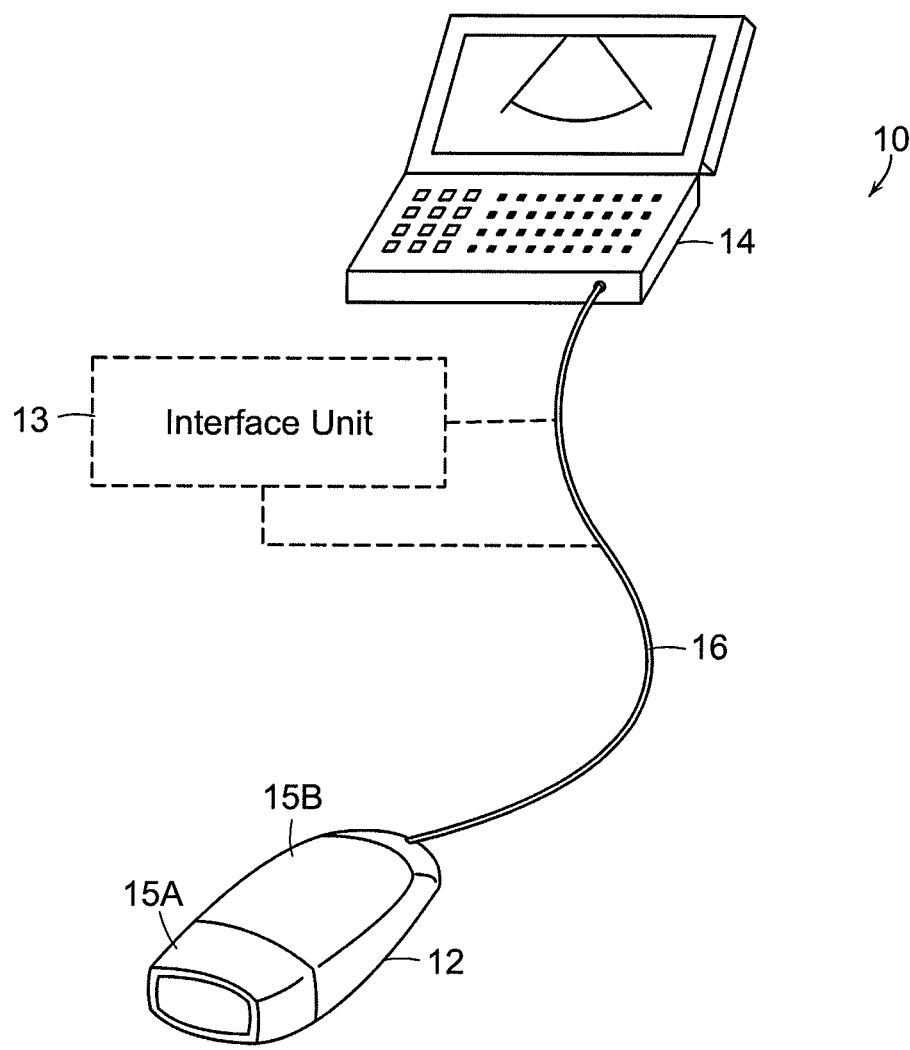
FIG. 10 illustrates a scan head connected to a portable computer in accordance with a preferred embodiment of the invention.

The invention can be implemented using a scan head 12 connected to a portable computer 14 as shown in FIG. 10. the ultrasound system 10 can also include a cable 16 to connect the probe 12 to the processor housing 14. Certain embodiments can employ an interface unit 13 which can include a beamformer device. Scan head 12 can include a transducer array 15A (2D) and a circuit housing 15B which can house multiplexer and/or beamforming components as described in detail in U.S. Pat. Nos. 6,106,472 and 6,869,401, the entire contents of these patents being incorporated herein by reference.

A 2D array configuration using sparse-array for transmission and non-overlapped fully-populated array is used for receiving. For an N×M element array, only m-elements with optimized sparse array placement are used for transmition and then the remaining NM-m elements are used as the receiving array. For example, for a 40×60-element 2D array, 256-elements are used as transmit element, the placement of the transmit elements are optimized based on selection criteria, the remaining 2144 element are used as received elements. This embodiment simplifies the multiplexer requirement needed for a 2D array, in which case the multiplexer can be mounted in the interface housing.

Figure 11:
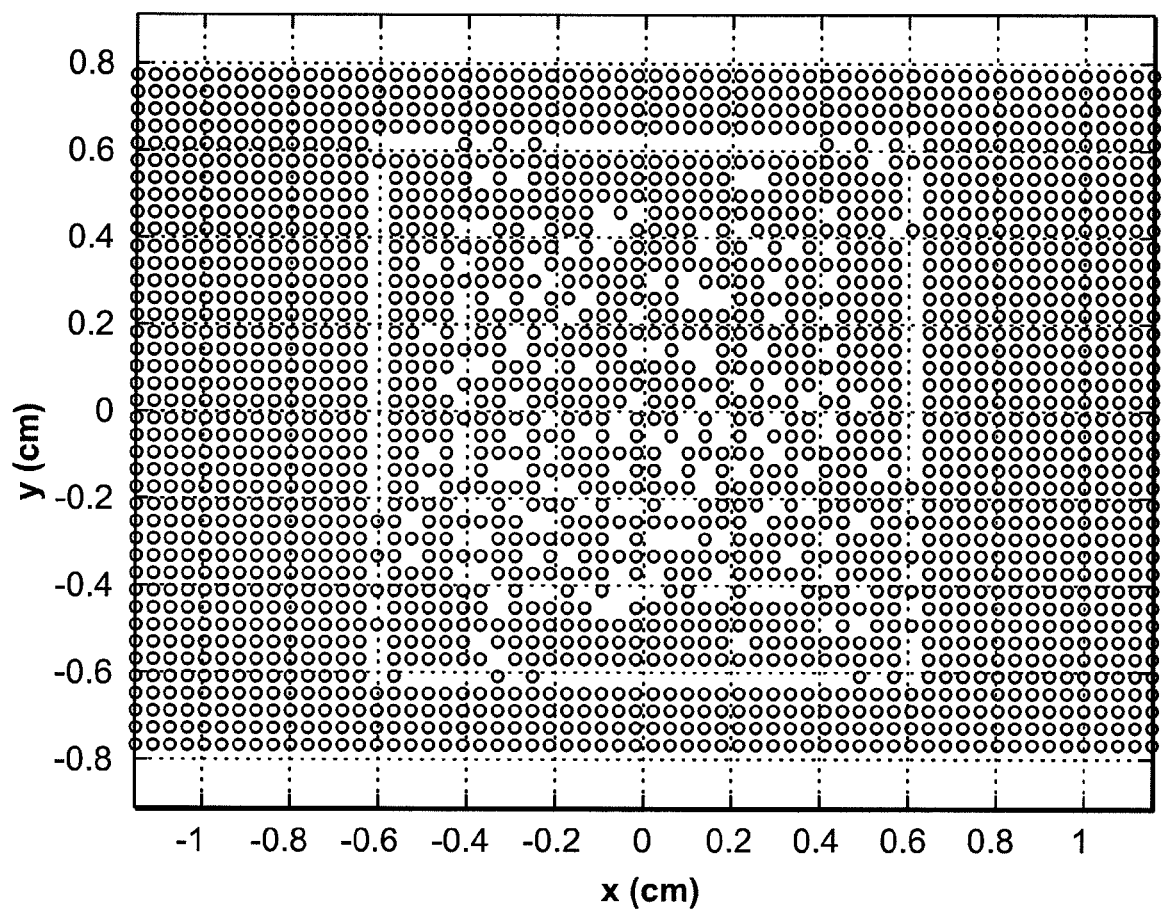
FIG. 11 illustrates a near fully populated receive array in which the receiving elements are independent of, and do not overlap, the transmit array.

An example of the element locations for the near fully-populated 40 by 60 receive array 50 is shown in FIG. 11. The 2400-element array is depopulated by the 256 sparse array transmit elements to yield 2144 receive element locations. These elements are independent and do not overlap the sparse-array transmit elements. In a preferred embodiment the transmit elements constitute less then 25% of the total number of array elements, and preferably less then 15%.

Figure 12:
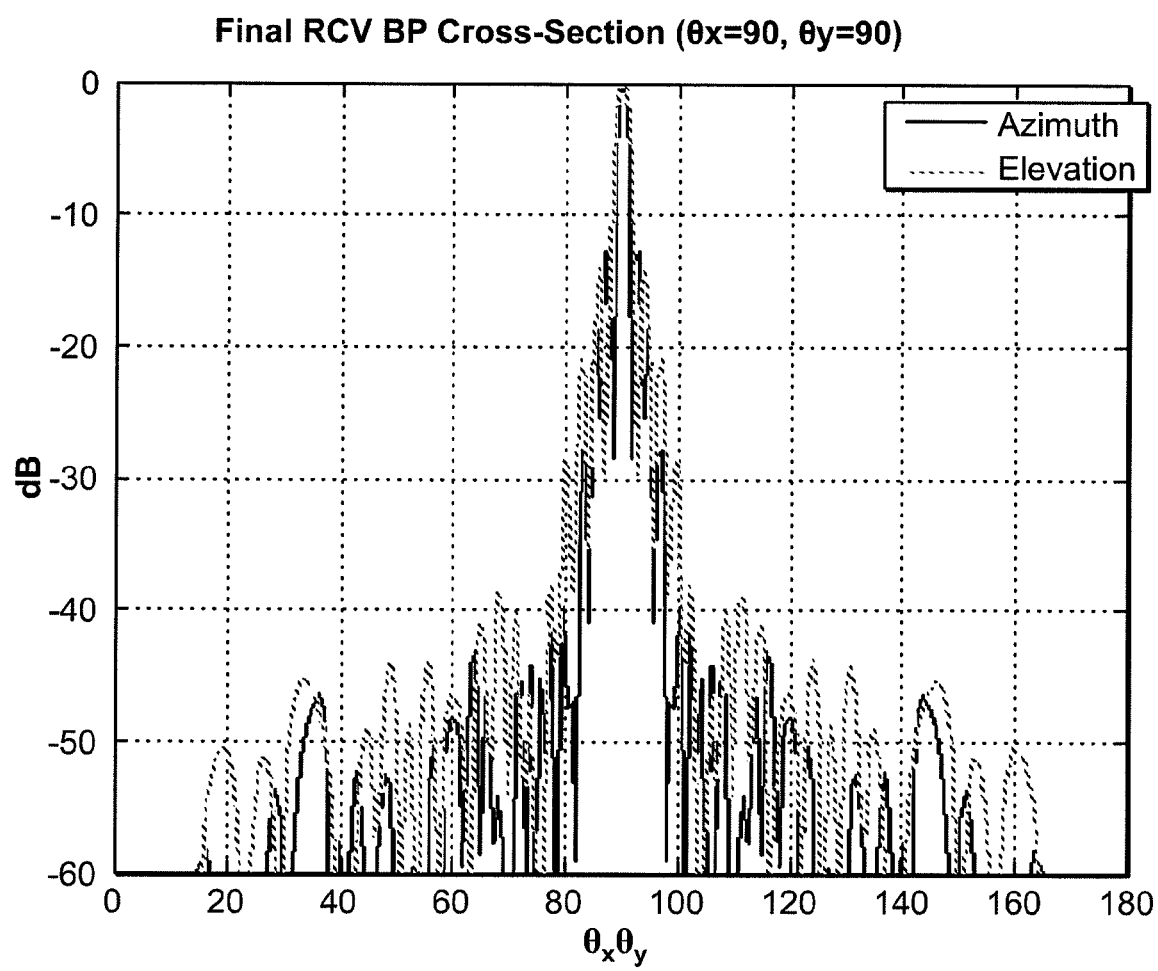
FIG. 12 graphically illustrates the azimuth and elevation cross-sections of the receive array beampattern.

The azimuth and elevation cross-sections of the beampattern of the above mentioned receive array are shown in FIG. 12. The first sidelobe is approximately −13 dB relative to the central peak. The grating lobes are less than −30 dB relative to the peak. Given that the 2D array is wider than tall, the azimuthal beamwidth (plotted in blue (solid)) is slightly narrower than the elevation beamwidth (plotted in green (dotted)).

Figure 13:
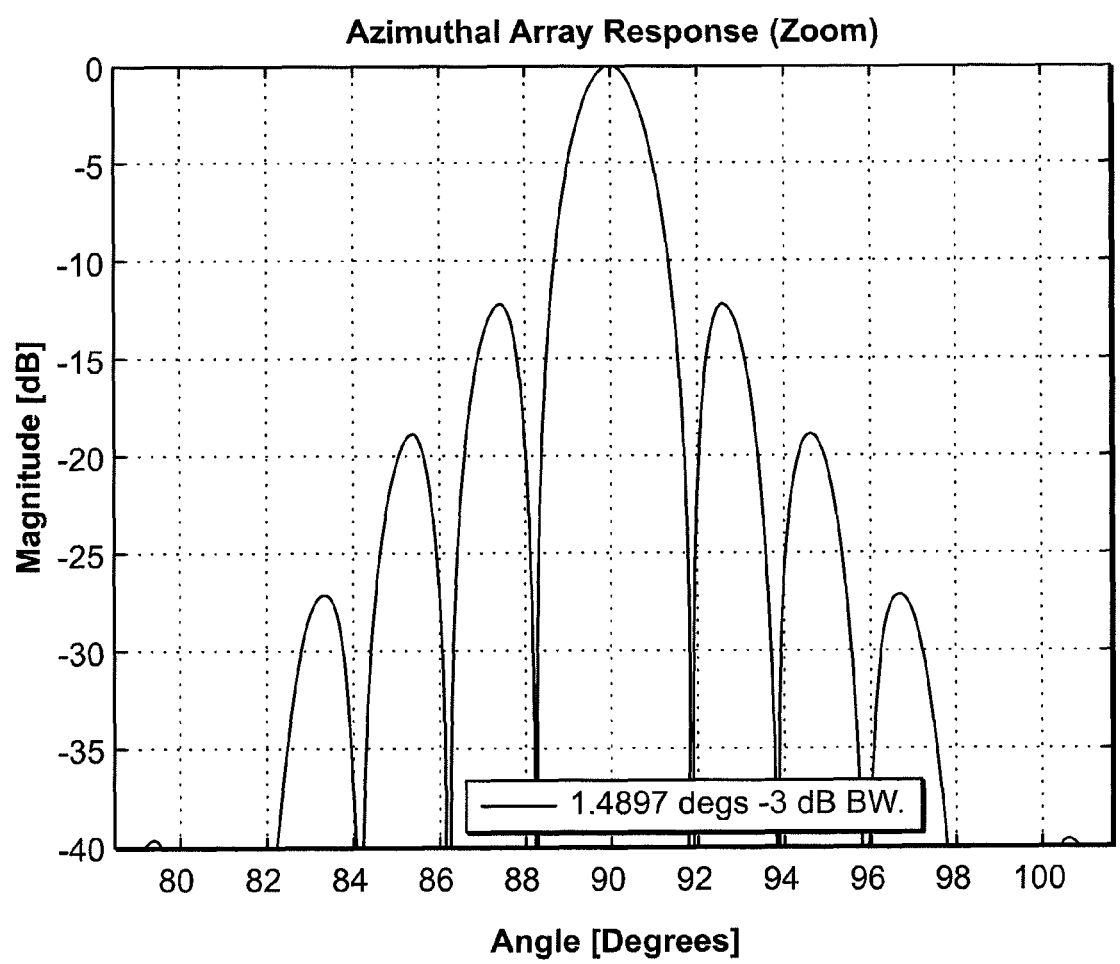
FIG. 13 is a magnified portion of the azimuthal beampattern of FIG. 12 showing the mainlobe and sidelobe structure.
Figure 14:
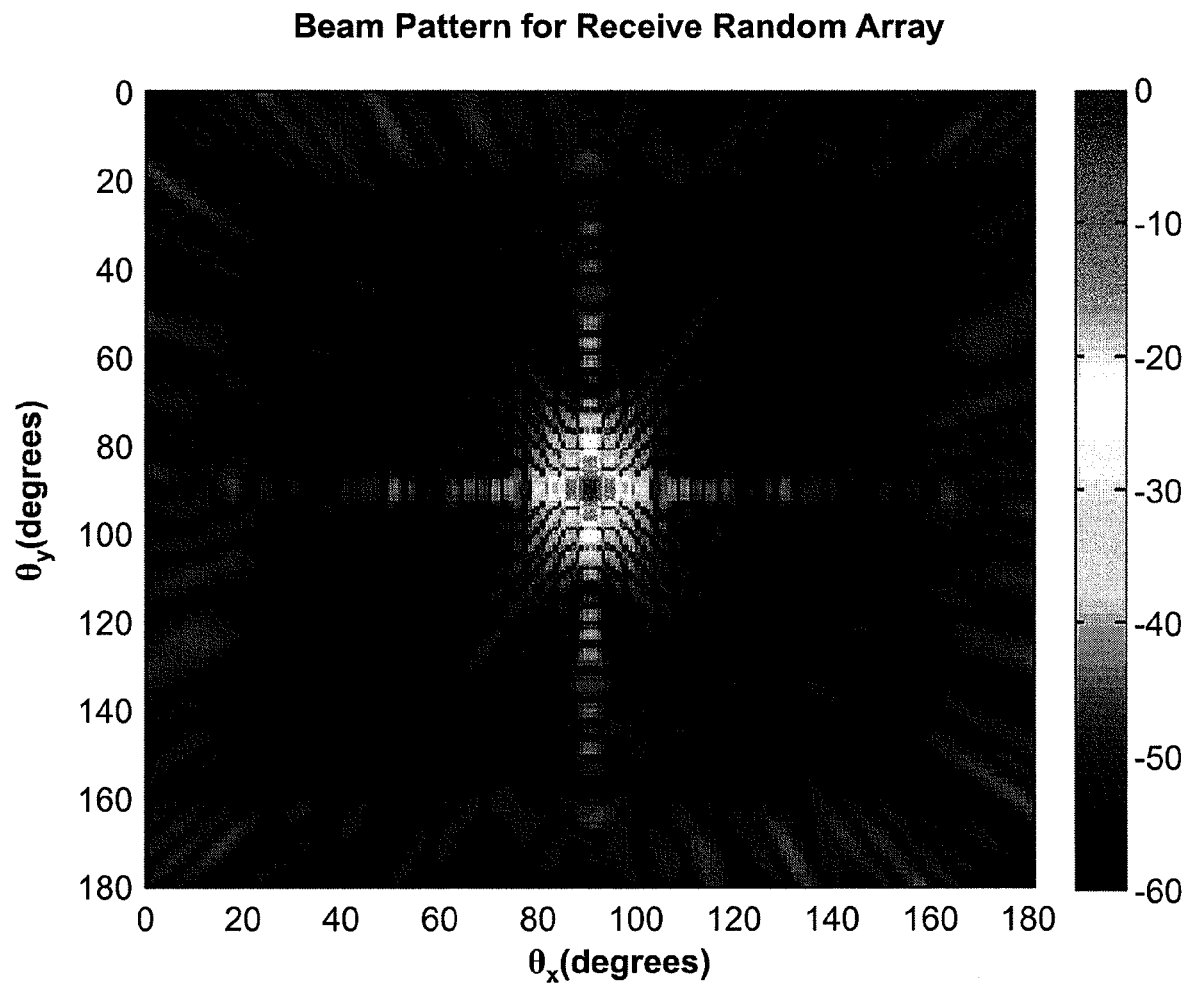
FIG. 14 illustrates a near fully populated receive array beampattern.

In FIG. 13, a magnifying view of the above mentioned azimuthal beam pattern, demonstrates the detailed mainlobe and sidelobe structure. For this case, the beamwidth is approximately 1.5 degrees. The beam pattern is nearly identical to the fully populated 60×40 element beam pattern. The receive array beam pattern is shown in FIG. 14. As stated above, the received sparse array is comprised of a 2144 elements. There are no sidelobes due to depopulating the center of the array by 256 (transmit) elements.

Figure 15:
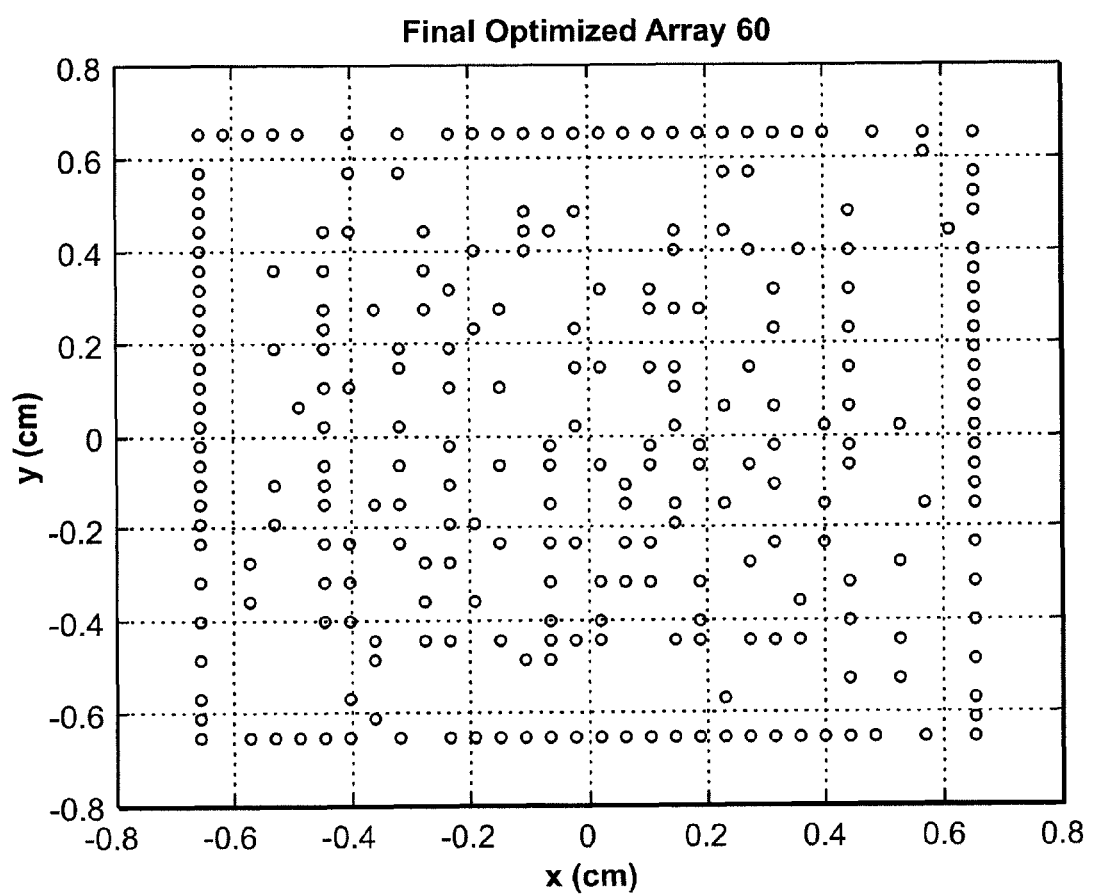
FIG. 15 shows selected transmit locations for a sparse array in accordance with the invention.
Figure 16:
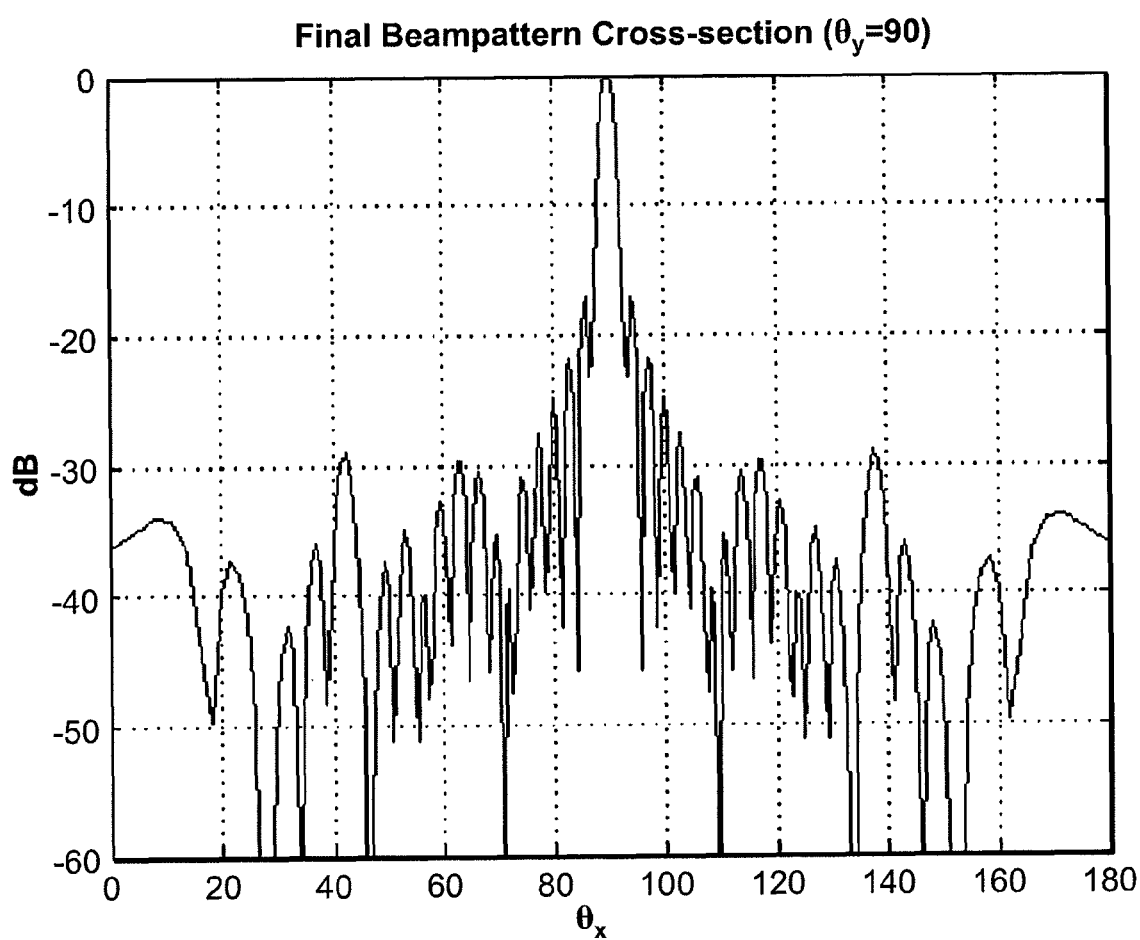
FIG. 16 illustrates a cross-sectional view of the transmit sparse array beampattern of the embodiment in FIG. 15.

An example of the final element locations for the 256 transmit sparse array 60 are shown in FIG. 15. The 256 element locations are confined to the central 32×32 elements of the fully populated array. These elements are independent and do not overlap the receive array elements. A cross sectional view of the transmit sparse array beampattern is shown in FIG. 16. The first sidelobe is approximately −17 dB relative to the central peak. The grating lobes are less than −27 dB relative to the peak. The sparse array optimization algorithm minimizes the sidelobe energy +/−45 degrees in elevation and +/−45 degrees in elevation.

Figure 17:
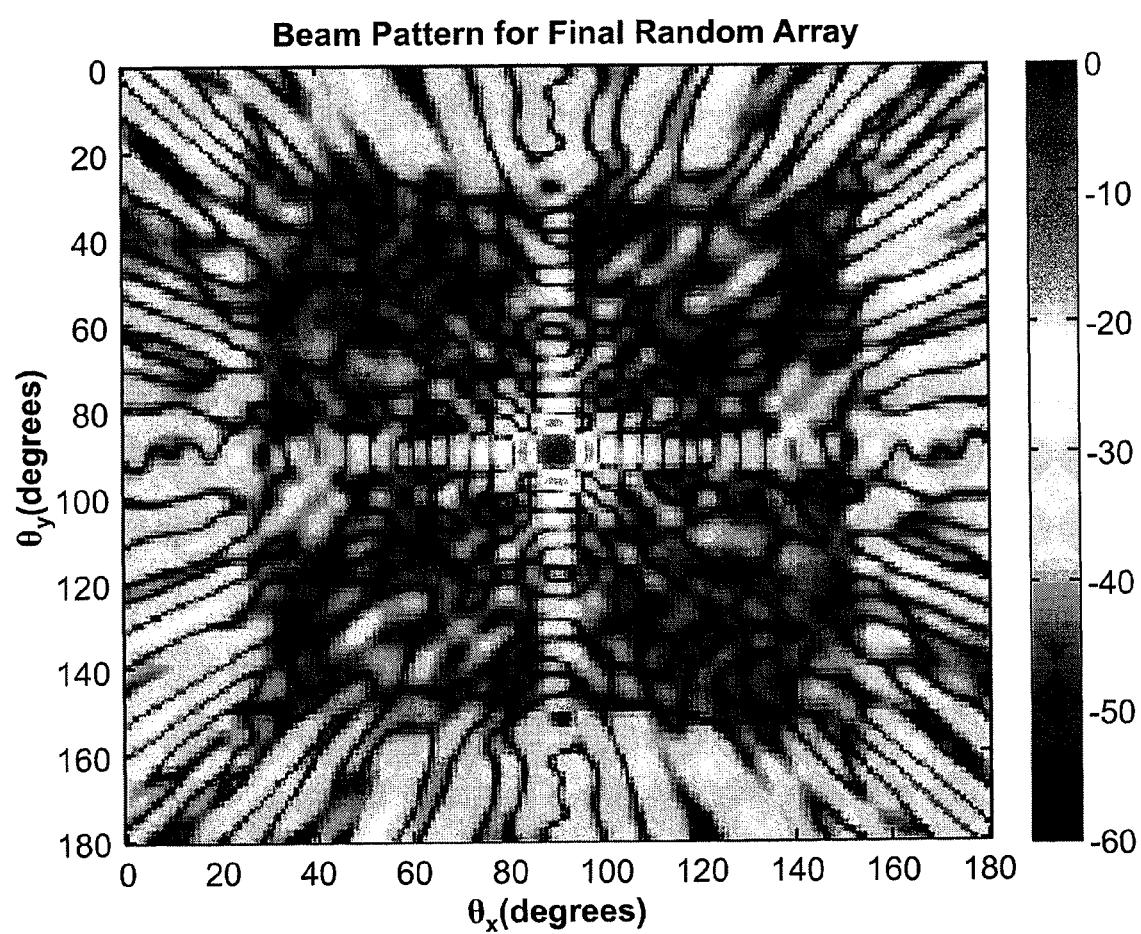
FIG. 17 illustrates a sparse transmit array beampattern.
Figure 18:
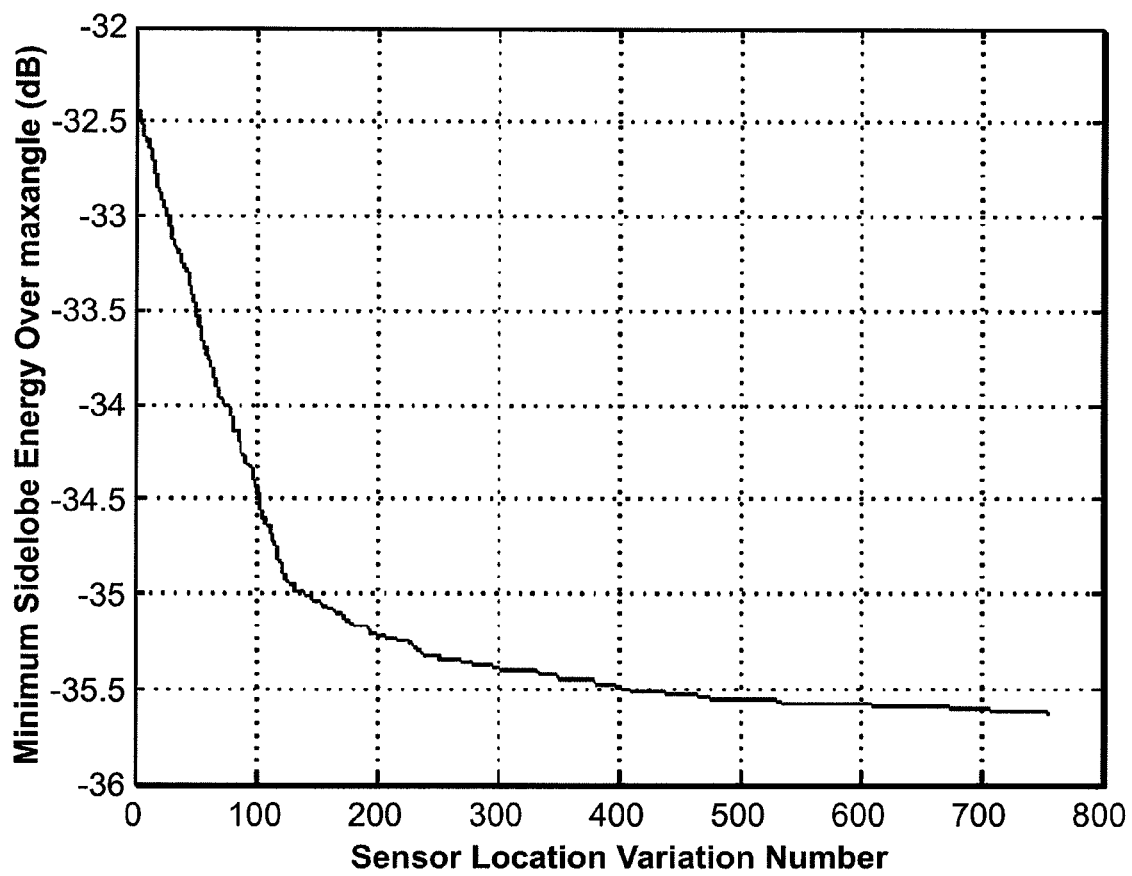
FIG. 18 illustrates that it is possible to limit average sidelobe energy to less than −35 dB relative to the central peak of the beampattern.

FIG. 17 demonstrates the beam pattern of the sparse transmit array shown in FIG. 15. The transmit beampattern is designed to uniformly cover a 4×4 beam data pyramid. The transmit sparse array is comprised of a 256-element subset of the fully populated 2400-element array (approximately 10% fill). The placement of the transmit/receive array design algorithm required over 750 iterations to minimize the transmit and receive sidelobe energy within the +/−45 degree azimuth, +/−45 degree elevation region. As shown in FIG. 18, after 750 iterations, the final sparse transmit-array element locations limit the average sidelobe energy to less than −35 dB relative to the central peak of the beampattern.

A low-power ultrasound system capable of electronically scanning a two-dimensional, 2D, matrix array to generate real-time three-dimensional, 3D, volumetric images with 64 by 64, 4096, scanning beams at a greater than 20 3D images per second is described. For each transmit pulse, the system is capable of generating 16 received beams. In addition, the design is able to drive a one and one-half dimensional array and also support wide-bandwidth encoded transmit waveform for pulse compressing to improve the system sensitivity. Wide bandwidth enables the use of chirped or coded waveforms (PN sequence) that can extend the length of the low power transmit burst without a loss of axial resolution. The combination of these features results in an imaging array with electronic systems that will fit within a portable hand-carried device.

The beamformer processing system is a time domain processor that will simultaneously process the returns of a large 2D array, the low-power; highly integrated beamformer that provide a real time processing of the entire array and will thus provide a low cost unit that can be hand carried.

There is a strong need for a real-time 3D ultrasound imaging using a 2D matrix array. In this section, the minimal number of receive beamforming channels required in an ultrasound system to support a real-time 3D imaging is analyzed. It is shown that a minimum of 192 parallel received beamforming channels is required to support a reasonable sized such as 48×64-element array.

An example of a system having an electronically-adjustable acoustic conformal lens is to divide the surface of a 2D transducer array into plane "tiles" of relatively small subarrays can be formed in U.S. Pat. No. 6,292,433, the contents of which is incorporated herein by reference; beamforming of the entire array can be separated into two stages, first a small-aperture subarray beamforming followed by a second stage large-aperture coherent summing of the outputs from each of the subarrays. As depicted in the tiles/subarrays can be made small enough so that when an object is placed within the field-of-view of the imaging system, the incident radiation from the object toward each "tile" can be treated using a far-field approximation. However, near-field beamforming capability has been incorporated in the actual implementation of the subarray beamforming system to allow a broader application. Additional delay elements are incorporated as second-stage processing to allow all subarrays to be coherently summed. The delay-and-sum beamformer allows each subarray to "look" for signals radiating from a particular direction. By adjusting the delays associated with each element of the array, the array's look direction can be electronically steered toward the source of radiation. The delay line requirement for each element in the sub-array can be less than a hundred stages. Only long delays for global summing are needed for the final near field focusing. A detailed diagram of an electronically-controlled beamforming system in accordance with the invention is shown in FIG. 14A of U.S. Pat. No. 6,292,433. This system consists of a bank of parallel time-delay beamforming processors. Each processor consists of two components: a 2D sub-array beamformer for small-aperture beamsteering/focusing and an additional time delay processor to allow hierarchical near-field beamforming of outputs from each corresponding subarray. As can be seen in FIG. 14A referenced above for a system with m-subarrays, m-parallel programmable $2^{nd}$-stage near field time delays are needed for individual delay adjustment to allow all m-parallel outputs be summed coherently, in turn, this summed output provides the 3D images of the targeted object.

It is easy to understand that, without using this hierarchical subarray small aperture and then large aperture beamforming approach, for an 80×80 element 2D array, a cable consisting of six thousand and four hundred wires is needed to connect the transducer array to a conventional beamforming system. As shown in FIG. 14A of U.S. Pat. No. 6,292,433 referenced above, the number of inputs to each subarray processor equals the total number of delay elements in the subarray, each sub-array only has a single output. That is to say, the number of inputs to a subarray equals the number of transducer elements associated with that subarray. The number of subarray outputs equals the total transducer array element number divided by the number of subarrays. For example, if one selects to use a 5×5 subarray to implement this hierarchical beamforming system, after the first stage subarray beamforming, the total number of wires needed to connect to the $2^{nd}$ stage near-field beamforming is reduced by a factor of 25. More specifically, as mentioned above, without using this 2D subarray beamforming, 6400 wires are needed to connect an 80×80 2D transducer array to a conventional back-end beamforming. Using a 5×5 subarray processing bank first, the number of wires required to connect to the backend beamforming system is reduced to 256. Based on this example of the invention, a bank of 256 5×5 element subarrays beamformer can be integrated with a 80×80 element 2D array in the scan head, so a cable consisting of 256 wires is adequate to connect the integrated scan head with the back-end near-field beamforming system.

It is important to note that 5×5 subarray small-aperture beamforming processors can be easily integrated in a small size silicon integrated circuit, eight of such 5×5 subarray beamforming can be integrated on one integrated circuit. Note that subarrays have generally between 9 and 64 transducer elements corresponding to a 3×3 subarray up to an 8×8 subarray. The preferred range is at or between 4×4 and a 6×6 array for a square array geometry. Rectangular subarrays can also be used preferably either 3×4, 4×5, or 4×6. Note that a ¼λ error minimum criteria is uses. Only 32 integrated circuit devices need be incorporated into the scanhead, it can reduce the cable size from 6,400 wires down to 256 wires. Similarly, for a 64×48 element 2D array, using a 4×4 subarray processing bank in the transducer housing first, the number of back-end beamforming channels is reduced to 192.

In the present invention, preferred embodiments for a 2D array beamforming, each minimizing noise and cable loss with improved signal to noise ratio performance, are described in FIGS. 4-6B. In these embodiments, the bank of m parallel subarray beamforming processors are integrated with the 2D transducer array to create a compact, low-noise, scan head. FIG. 4 depicts a system that the compact scan head is connected to a dedicated processing module, in which the m-parallel preamp/TGCs, transmit/received chips and the $2^{nd}$ stage time delay processing units are housed. This dedicated processing module communicates with a host computer 540 via FireWire, USB or PCI bus. Control and synchronization is preformed by the system controller located in the processing module. FIG. 5 depicts the same architecture as stated in FIG. 4, except, inside the dedicated processing module, the $2^{nd}$ stage time delay processing units are specifically implemented by using Charge-Domain programmable time-delay lines. FIGS. 6A and 6B depicts a system that the compact scan head is connected to a conventional, commercially available time-domain digital ultrasound imaging system with m-parallel beamforming channels. It is easy to see that in FIGS. 6A and 6B the time-delay processor can also be implemented by using CDP time-delay lines.

In a preferred embodiment of the system a large-aperture beamforming system is incorporated into the main processor housing of the ultrasound imaging system as shown in connection with FIGS. 19-24B.

The speed of sound in tissue is about 1500 cm/sec so that the round-trip propagation time for a sound wave penetrating a 15-cm depth is about 20 microseconds. For a real-time 3D imaging, at least 64×64 scanning beams at a frame rate greater than 20 3D volumetric images per second are needed to provide diagnostic quality images. For each transmit beam, the real-time 3D imaging system has to be able to form at least 16 beams for each transmit pulse to support the preferred 3D frame rate requirement. In this section, both a serial time-multiplexed beamforming and a parallel simultaneous time-domain beamforming implementation are addressed.

To achieve a 16 beam scanning requirement, a combination of serial and parallel architecture can be used, i.e., the system can use front-end time-multiplexed serial beamforming elements technique to form two beams, then followed by 8 parallel beamforms at the back-end processor, or the system can form 4 serial beams, for each serial output beam, the back-end processor then forms 4 parallel beams, and so forth.

By systematically varying beamformer delays and shading along a viewing angle of a 2D transducer array, returned echoes along the line of sight representing the 3D radiation sources can be used to create the scanned image at the scanned angle. The system can provide continuous real-time large area scanned images throughout a large field of view at 20 frames/s or more. As shown in FIG. 7, in a CDP beamforming chip, a time multiplexed computing structure can be used to generate multiple beams, i.e., for each transmit pulse, the bank of 2D subarrays and its corresponding $2^{nd}$ stage near-field time-delay line are capable of providing multiple beams sequentially. The computing circuits sequentially generate the delays required for forming K beams. The device operates using the following sequence: once a set of sampled returned-echoes are loaded in the delay lines, at time $t_1$, the delays required for forming beam 1 are computed within each module and applied in parallel to all delay lines. The sampled return-echoes with proper delays are coherently summed to form the first beam. At time $t_2$, the delays required for forming beam 2 are computed within each module and applied in parallel to all delay lines. The sampled return-echoes with proper delays are coherently summed to form the second beam. The procedure repeats until the Kth beam is coherently formed.

For example, if a computing circuit with 16-serial addressable outputs is incorporated with the processor subarray and the $2^{nd}$ stage time delay lines, for each transmit pulse, 16 beams or scan lines each along a different scan angle can be created. For 256-pulses with a down-range depth of 15 cm, the system can generate a 4096-beams with a 64×64 pixel resolution at a frame rate of 20 frames/s. The system is fully programmable; the beamforming electronics can be adjusted to zoom-in to a smaller field-of-view for high-resolution or higher frame rate images. For example, using 192-transmit pulses with the same down-range depth of 15 cm, the system can generate a 3072-beams with a 64×48 pixel resolution at a 30 frame/s frame rate.

The objective of a beamforming system is to focus signals received from an image point onto a transducer array. By inserting proper delays in a beamformer to align wavefronts that are propagating in a particular direction, signals arriving from the direction of interest are added coherently, while those from other directions do not add coherently or cancel. The time-of-flight from the radiation source to the focal point can be calculated and stored in memory for every channel from multiple directions of arrival in parallel. In a conventional implementation, separate electronic circuitry is necessary for each beam; for a multi-beam system, the resulting electronics rapidly become both bulky and costly as the number of beams increases. For example, beamforming for a linear 192 element array requires 192 parallel delay lines each with a programmable delay length of greater than 128λ. To form four parallel beams, for example, a total of 768 programmable long delay lines are required. To simplify the required electronics for multiple beams, a hierarchical two stage beamforming system is described.

Figure 19:
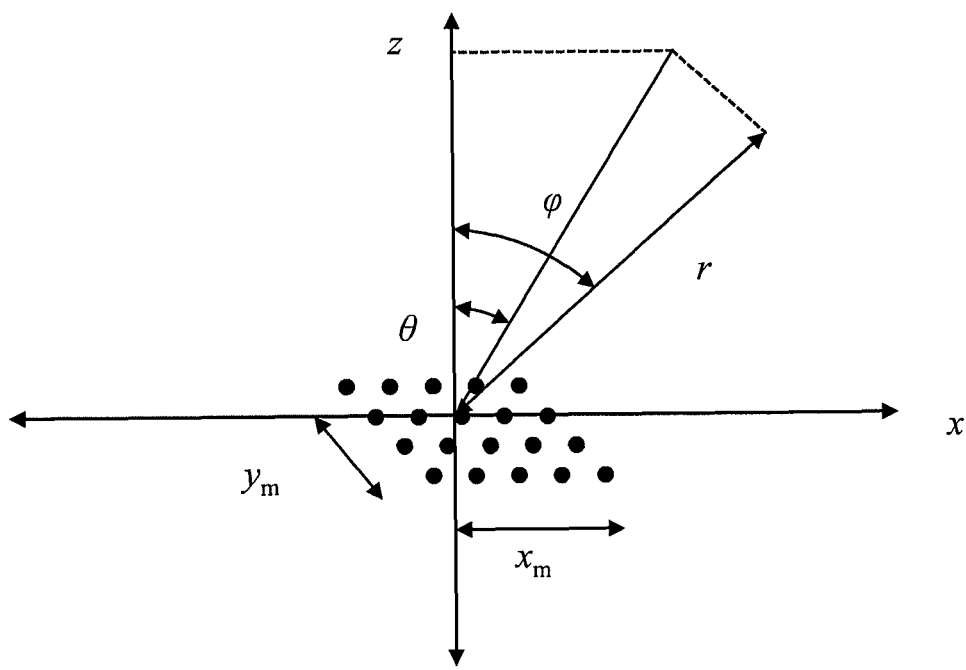
FIG. 19 illustrates the 2D differential delay equation.

The concept of hierarchical beamforming is to separate the time-of-flight calculation into two parts: the first part is a short delay for coarse-resolution, small aperture beamforming, followed by a long delay for fine resolution, large aperture beamforming. Shown in FIG. 19 is the 3D differential delay equation for a 2D array. This equation represents differential delay at array element $(x_m, y_m)$ as a function of range and angles Theta and Phi (relative to the center of the 2D array). The equation can be reduced to a 1D array by setting all of the $y_m$ (y coordinates of the element locations) to 0. The differential delay can be constrained to a single plane (instead of a volume) by setting angle Phi=0.

Figure 20:
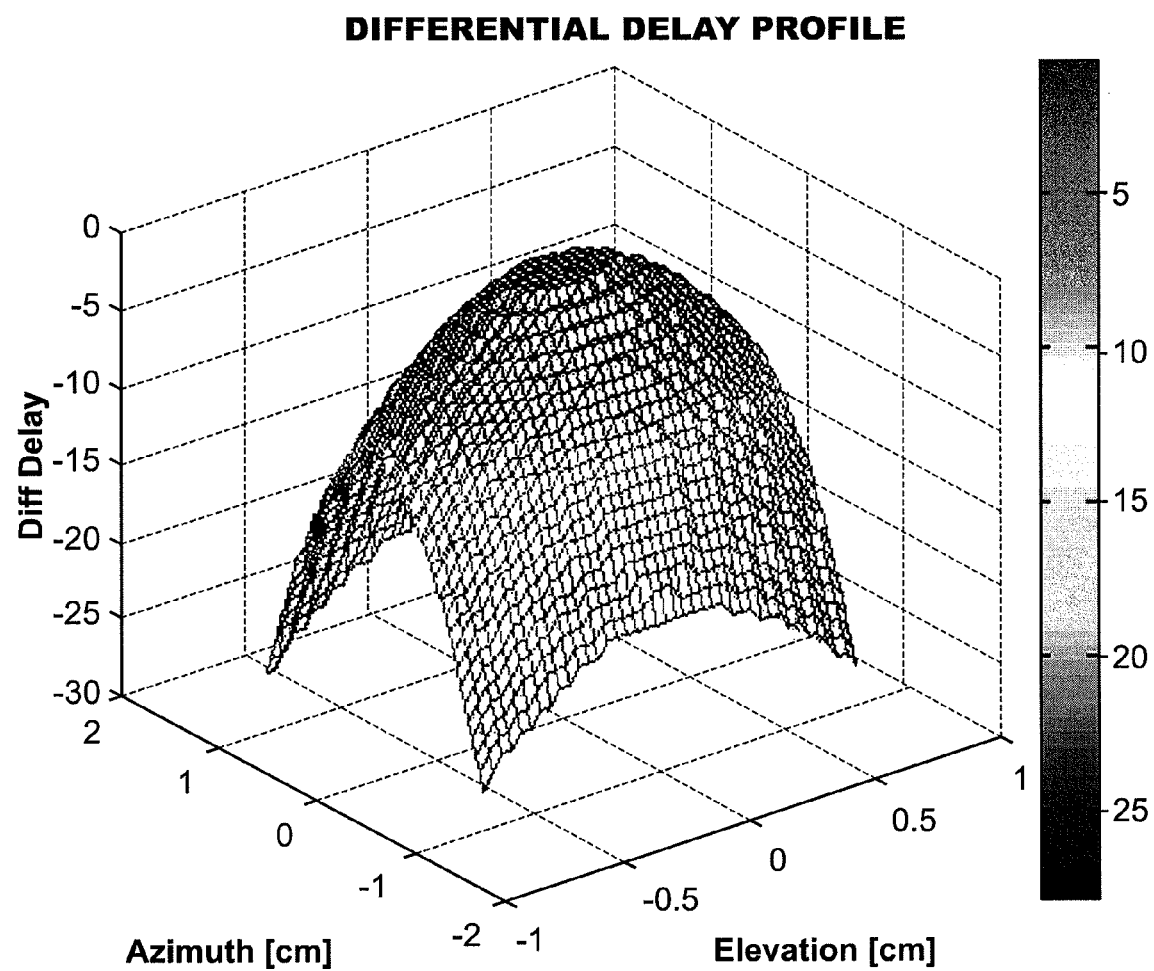
FIG. 20 illustrates a differential display profile.

To exemplify operation of a two-stage delays, a differential delay profile must be generated for all elements in the 1D or 2D array. To do this, the differential delay equation is calculated and all of the differential delays as a function of angles Theta and Phi, at a given range, are tabulated. For example, as shown in FIG. 20, the differential delay profile is plotted for an element near the center of a 2D array.

Figure 21:
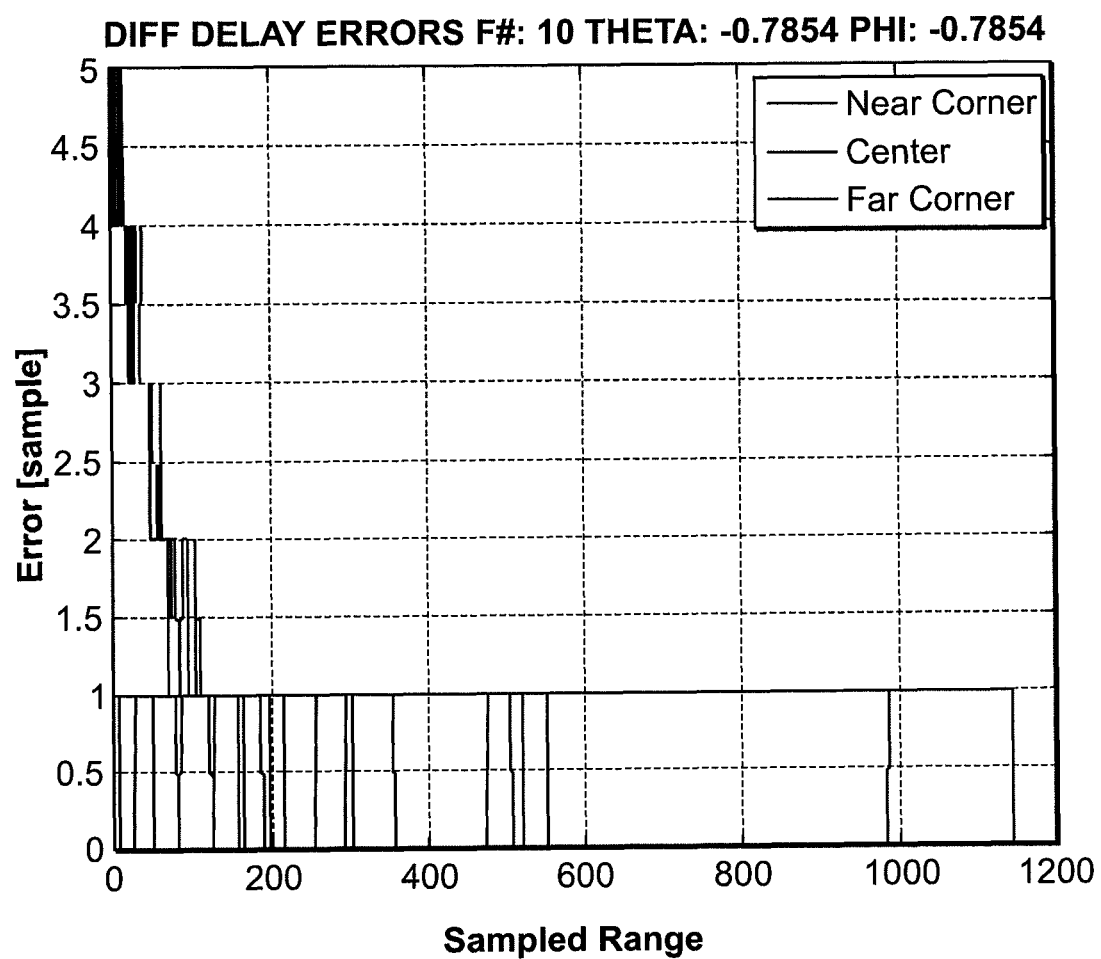
FIG. 21 illustrates differential delay errors.
Figure 22B:
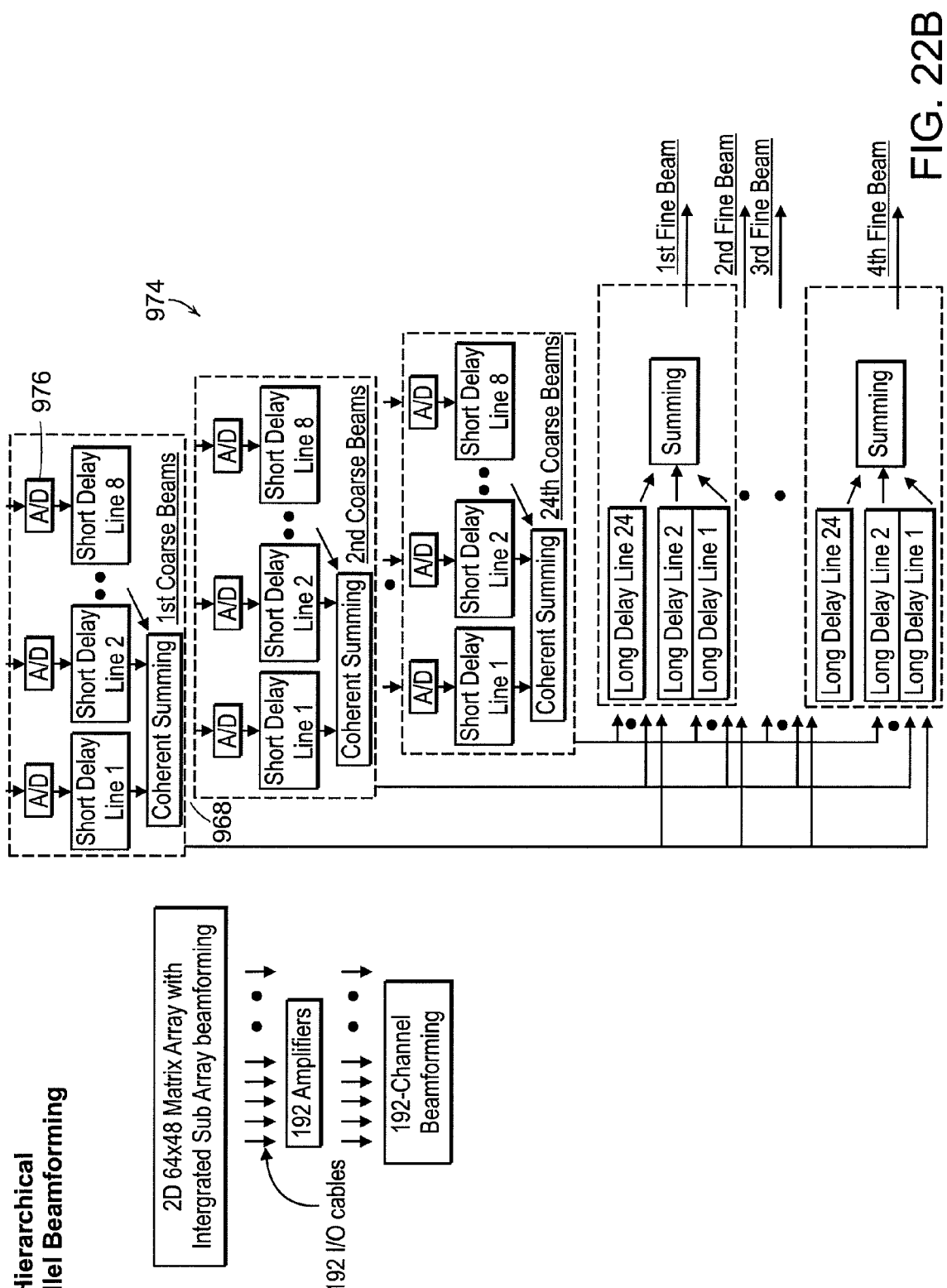

In a 2 stage delay system, the tabulated data from the preceding step are broken into a coarse delay and a fine delay. To determine how to partition the coarse delay and the fine delay, the maximum differential delay error is constrained (typically set to have a maximum differential delay error less than or equal to 1 sample). The tabulated delays (from the preceding step) are also used to determine when a receive element is enabled. For example, FIG. 21 depicts the differential delay error as a function of range for a few elements. The worst case differential delay (the data plotted in blue) is for an element in the corner of a 2D array (Theta=+45 degs, Phi=+45 degs) attempting to receive image data from the direction Theta=−45 degs, Phi=−45 degs. For this case, the maximum differential delay is greater than the constraint (>1 sample error); therefore, the element would not be enabled to receive until a range greater than approximately 100 samples.

A block diagram of an hierarchical two-stage parallel beamforming system 958 is shown in FIG. 22A. A two dimensional transducer array 960 of a handheld probe, such as 12 in FIG. 10 weighing less than 15 lbs, can be coupled to amplifier 962 before being connected to the input of the beamforming system 964. The beamforming system can comprise a plurality of short delay lines, which are coherently summed at summing circuit 968 where the output is delivered the longer delay lines 970, which are also summed at summing circuit 972. First stage coarse beamforming includes coherently summing returned echoes from a small aperture, for example, with 8 neighboring receivers in this particular embodiment. Because of the small size of the aperture, the delay length of each short delay is only about 8λ. So, for a 192 element inputs, 24 such small aperture, coarse beams are formed. Each of those 24 beams is then applied to its corresponding long programmable long delay line for a large aperture, fine-resolution beamforming. To form four parallel beams, four such beamforming structures are required. As can be seen in FIG. 22A, this hierarchical implementation to form 24 coarse beams, only 192 short delays are required, and then followed by 24 long delays, each one with a programmable delay length shorter than 128λ. For four parallel beams, only 192 short delays plus 96 long delays are needed, it offers a tremendous saving in terms of electronic components and power.

Furthermore, within each small-aperture, short-delay line, a time-of-flight control circuit is used to select the tap position output from a charge-domain processing circuit that nondestructively senses the tapped-delay line output. Each receiver has a multiplier for beam shading/apodization. Within each processor, all the multipliers share a common output. The summed charge is then applied to a matched filter to decode and to compress the returned echoes to produce an imaging pulse with a reduced signal-to-noise ration. An analog to digital (A/D) or a converter on-chip charge-domain A/D converter can be used so that hierarchical summing can be carried out digitally.

In a preferred embodiment, it is important to employ high speed digital communication connection between the beamformer output and the backend processor. As described previously, the analog returned echoes received by each transducer element is converted to a digital signal by an analog to digital converter (A/D) during signal processing. As shown in the beamformer 974 of FIG. 22B, A/D converters 976 can be used at the input of each short delay line and the time delays performed digitally. Or alternatively, as shown in the embodiment 980 of FIG. 22C, the A/D converters 982 can be used at the output of each coarse beam and the long delay can be performed digitally. The A/D conversion can be performed using available discrete components, or in a preferred embodiment, a charge domain A/D converter can be formed on the same integrated circuit with the charge domain beamformer with hierarchical summing carried out digitally.

Figures 23A, 23B:
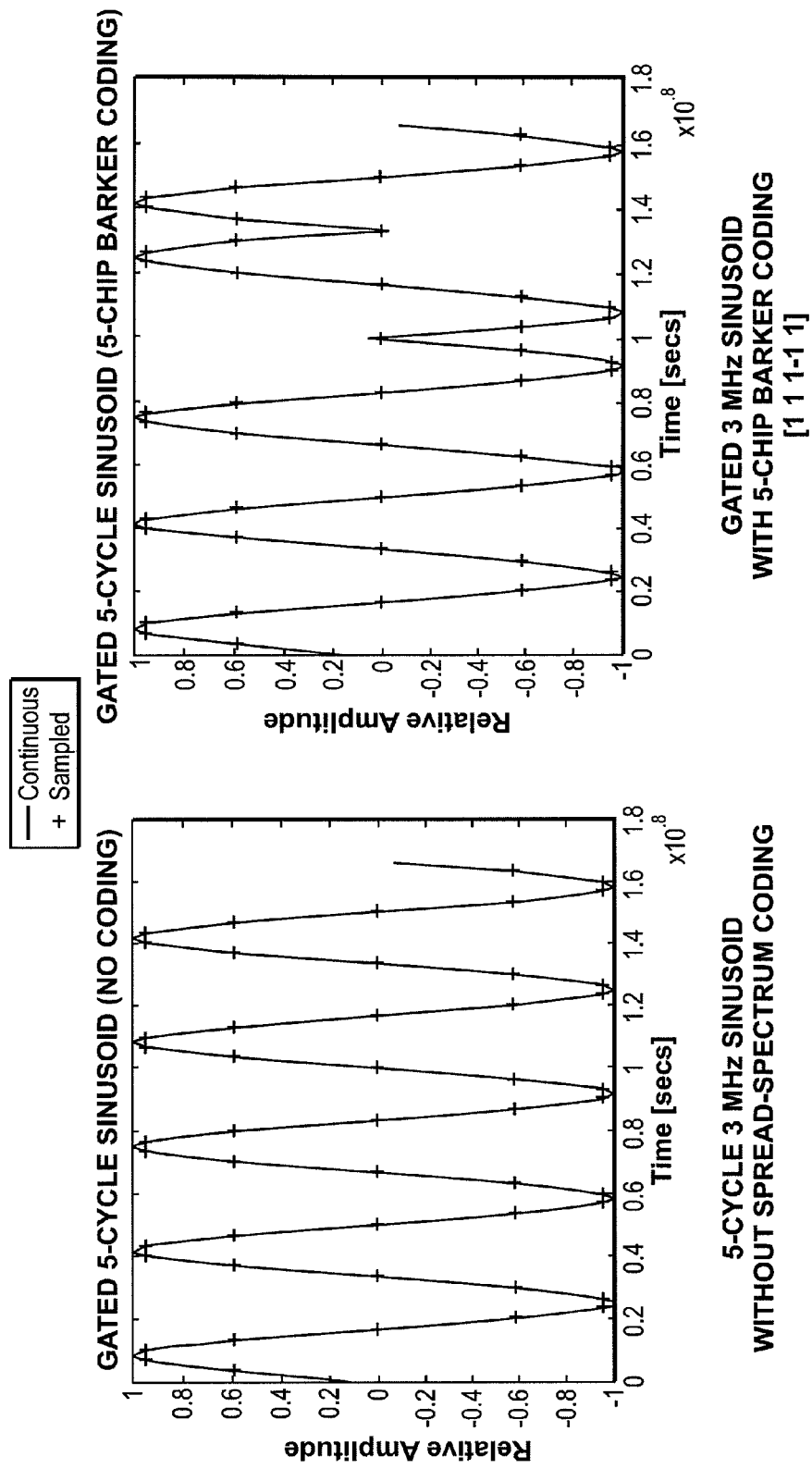
FIGS. 23A and 23B illustrated non-coded and coded transmit waveforms for spread spectrum ultrasound transmission.

The use of coded or spread spectrum signaling has gained tremendous favor in the communications community. It is now routinely used in satellite, cellular, and wire-line digital communications systems. Shown in FIG. 23A is an example of a 5 cycle 3 MHz sinusoid without spread spectrum coding. A coded or spread spectrum system transmits a broadband, temporally elongated excitation signal with a finite time-bandwidth product. The received signal is decoded to produce an imaging pulse with improved signal to noise ratio. The benefit of using coded signals in ultrasound imaging systems offers the use of high-resolution imaging while significantly lowering the peak acoustic power. These signals also provide signal processing gain that improves the overall system receiving sensitivity. Direct sequence modulation is the modulation of a carrier by a code sequence. In practice, this signal can be AM (pulse), FM, amplitude, phase or angle modulation. It can also be a pseudorandom or PN sequence that can comprise a sequence of binary values that repeat after a specified period of time.

In ultrasound, the concept of using spread spectrum/coded excitation transmit waveform comprises modulating a base sequence of transmit pulses of length P with a code sequence with a code length N. A code pulse sequence of N bursts is often referred to as an N-chip code. An example of a gated 3 MHz sinusoid with a 5-Chip Barker coding [111-11] is shown in FIG. 23B. Each "chip" corresponds to 1 cycle of the gated transmit waveform. Thus, FIG. 23B appears nearly identical to that of FIG. 23A except that the $4^{th}$ cycle is inverted. In both FIG. 23A and FIG. 23B, the continuous line represents the continuously sampled sinusoidal waveform, whereas the cross hatched points is a sampled signal, where 10 samples are taken per cycle. The coded pulse sequence, which has a length N×P, can effectively reduce the peak power in the transmitting media by spreading the power spectrum over a longer time duration. Upon reception of the spread spectrum/coded returned echoes, a pulse compression matched filter can be used to decode the received signals to produce an imaging pulse that has improved signal to noise ration (SNR). The SNR improvement of a N×P coded pulse sequence is 10 log(NP). So, for a Barker code of length 7 and a two-cycle burst transmit waveform, a SNR of 11.4 dB improvement can be achieved. However, in the present system, the transmit and received waveforms are oversampled with an oversampled rate of S. Typically an oversampled rate of S=4 has been used. It follows then, at the receiver end, a matched filter with tap length of N×P×S can be used to decode and to compress the returned echoes to produce an imaging pulse with a SNR improvement of 10 log(NPS). In the above example, for N=7, P=2, S=4, a SNR of 17.5 dB can be achieved.

Figure 25A:
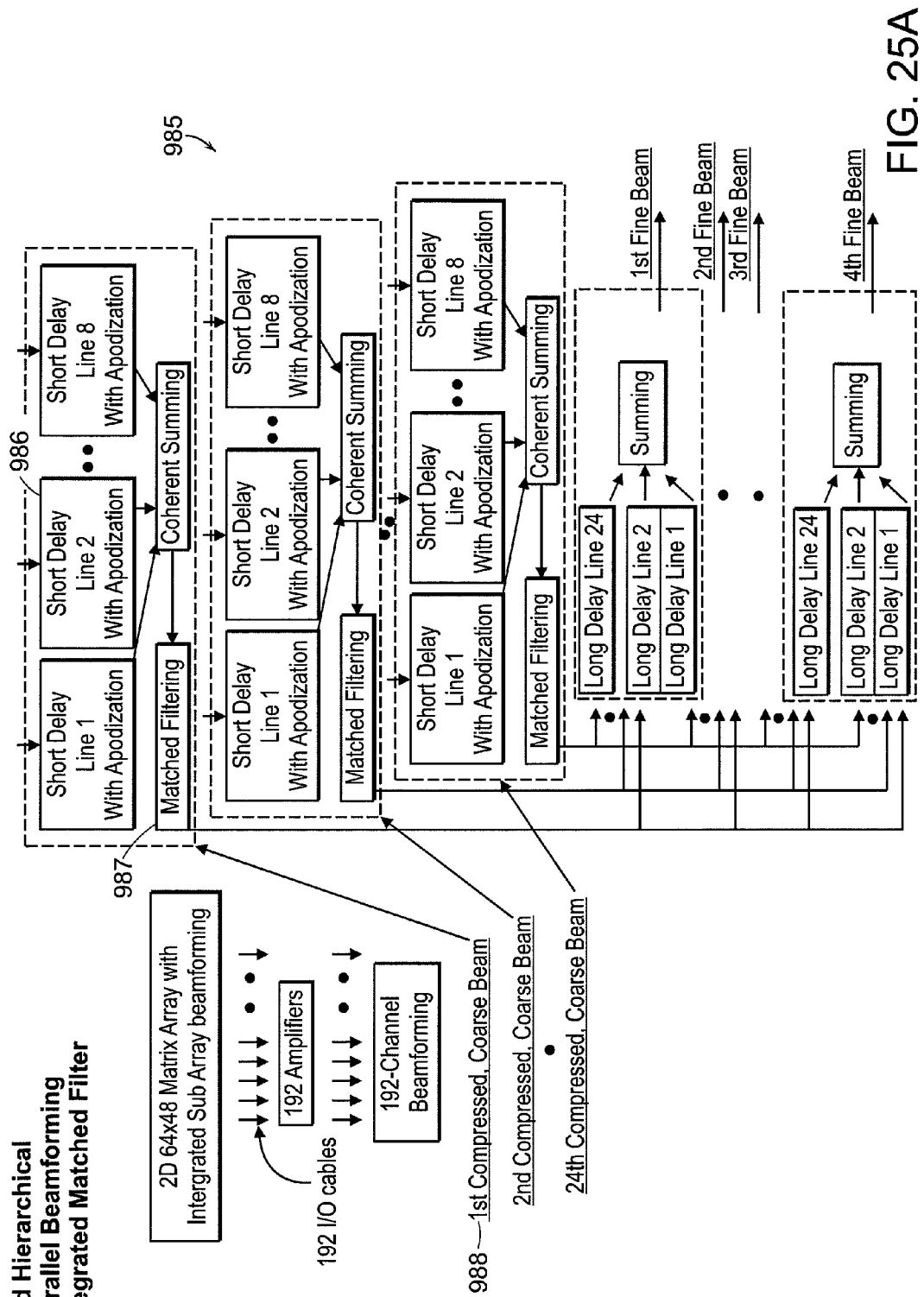
FIGS. 25A-25D illustrate preferred embodiments including a matched filter.
Figure 25B:
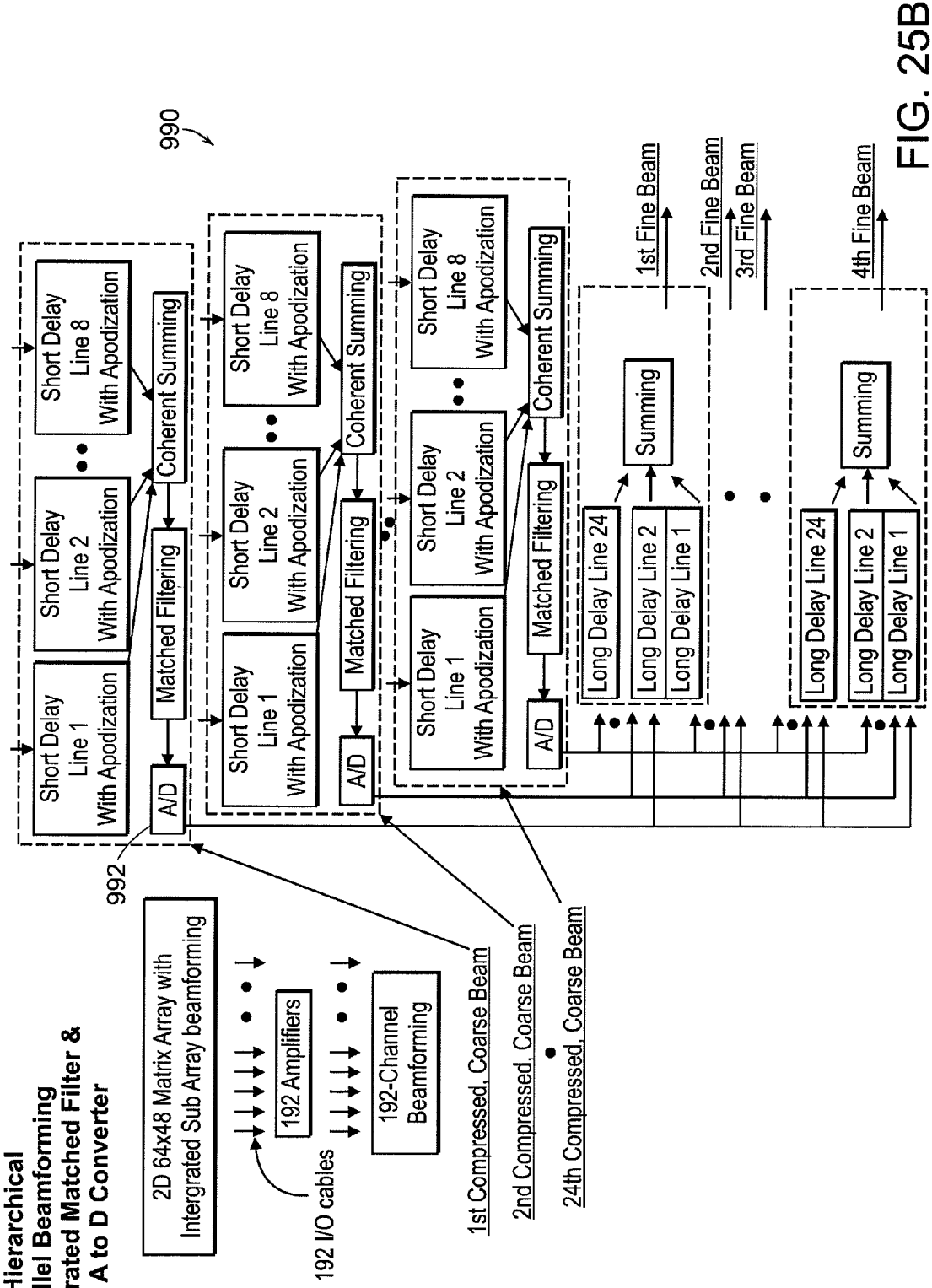

A preferred method of forming a transmission signal is shown in FIGS. 24A-24C. The base sequence is a single pulse, as can be seen in FIG. 24A. Using the 5-chip Barker code [111-11], FIG. 24B represents the convolution of the base sequence with the Barker code. Finally, the system transmits an oversampled version of the continuous waveform, as shown in FIG. 24C, a 6-times oversampled waveform is used as transmitted wave from A 192 channel receive beamforming system capable of forming four parallel, compressed beams for each transmitted, spreaded coded excited waveform is shown in the beamformer system 985 of FIG. 25A. In this implementation, a two-stage hierarchical beamforming architecture is used, first a small aperture short delay beamformer 986 output signals that are coherently summed return echoes from 8 adjacent transducers, a pulse compression matched filter 987 is then followed to decode the received signal, this compressed signal 988 is then applied to a long delay line to complete the beamforming requirement. In system 990 of FIG. 25B, an A/D converter 992 is incorporated at each of the matched filter outputs. It follows then the long delay will be carried out digitally, using a second stage digital delay line implementation.

Figure 25C:
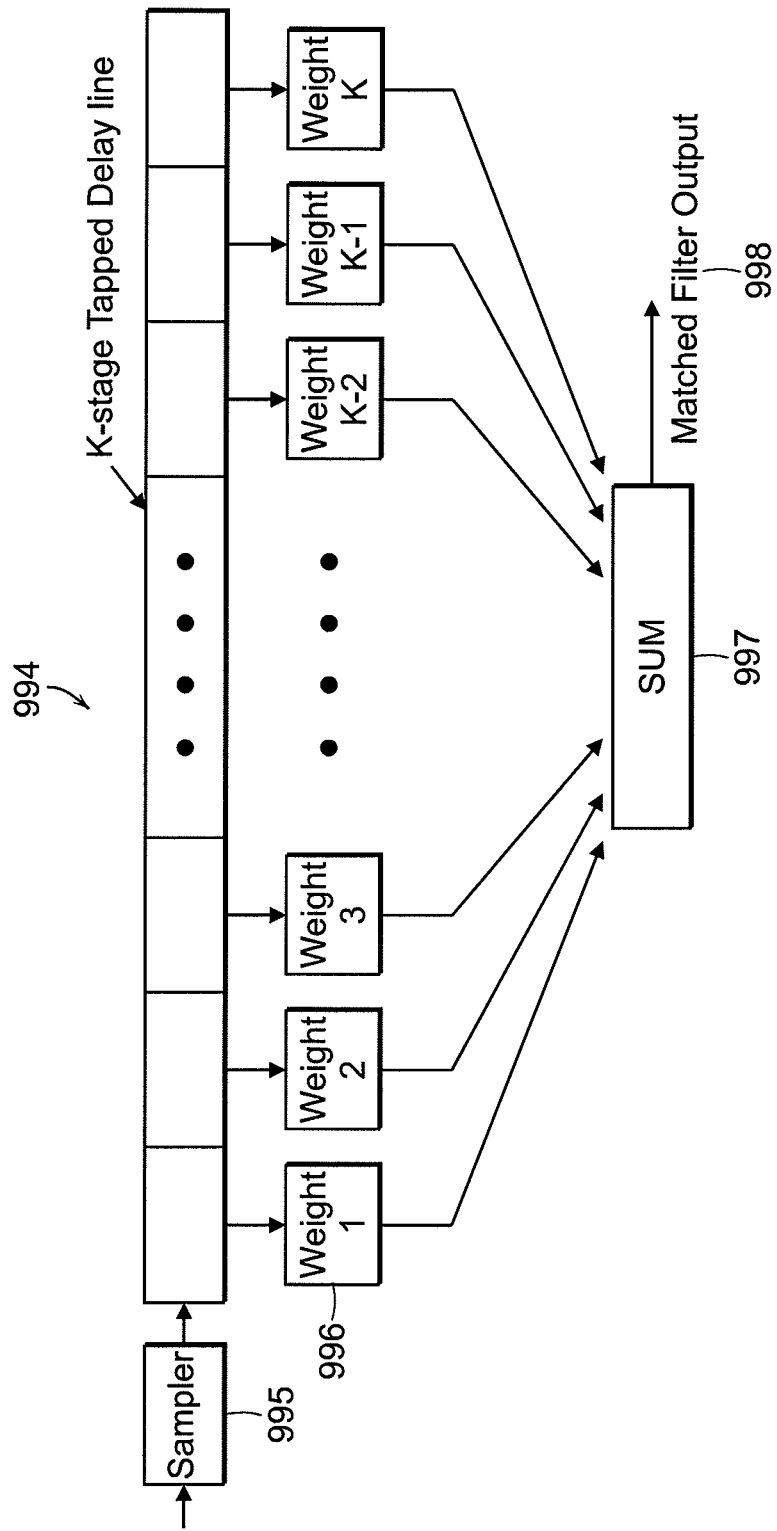

A matched filter implementation is shown in FIG. 25C. The filter 994 consists of a K-stage tapped delay line receiving signals from sampling circuit 995 and K programmable multipliers. The spreaded, coarse beamformed signal, $f_n$, is continuously applied to the input of the delay line. At each stage of the delay, the signals can be non-destructively sensed and multiplied by a tap weight 996, $W_k$, where k=1, 2, 3, ..., K−2, K−1, K. The weighted signals are summed together with summing circuit 997 to create a compressed output $g_m$ 998. It can be seen that, at time t=n, $$g_n = f_{n-1}W_1 + f_{n-2}W_2 + f_{n-3}W_3 + \ldots + f_{n-K-2}W_{K-2} + f_{n-K-1}W_{k-1} + f_{n-K}W_K$$

Figure 25D:
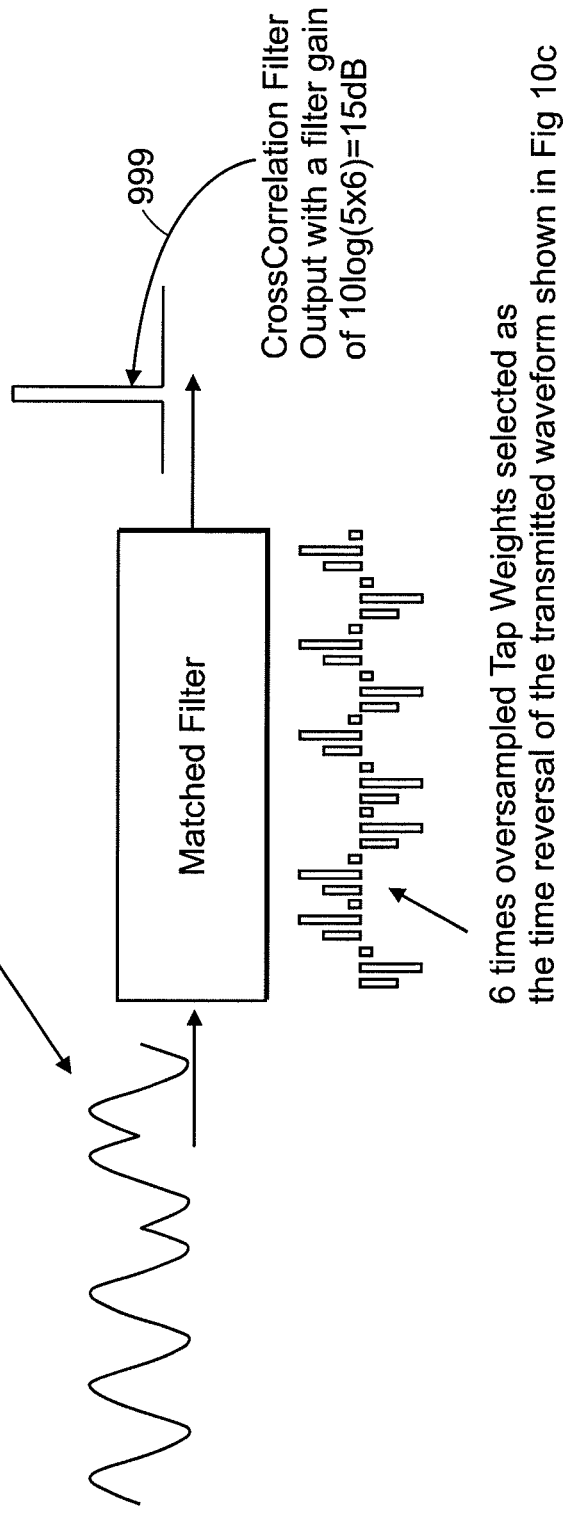

Using the example shown in FIGS. 24A-24C, if the system transmit a 6-time oversampled, 5-chip Barker code, and the weights of the matched filter are selected as a time reversal of the transmitted 5-chip Barker code excitation waveform, the matched filter produces a cross correlation output 999 that is the compressed, decoded pulsed signal (see FIG. 25D), with a filter gain of 10 log(5×6)=15 dB.

The claims should not be read as limited to the recited order or elements unless stated to that effect. All embodiments that come within the scope and spirit of the following claims and equivalents thereto are claimed as the invention.

What is claimed is:

1. A hand portable 3D medical ultrasound imaging system comprising:
   a two dimensional array of transducer elements in a transducer probe housing, the transducer probe housing having a programmable delay selection circuit and a first beamformer device generating coarse image data;
   a second beamformer device and a subarray processor in a second processor housing, the second beamformer device being in communication with the probe housing, the second beamformer device receiving coarse image data from a first subarray and having a first plurality of fine delay lines that receive first coarse image data, the second beamformer device receiving coarse image data from a second subarray with a second plurality of fine delay lines, the first subarray and the second subarray operating in parallel to provide three dimensional image data in response to the subarray processor, the second processor housing having a system controller and a data processor that performs scan conversion and Doppler processing operations, the second processor housing being connected to the transducer probe housing with a cable, such that the system weighs less than 15 lbs.

2. The system of claim 1 further comprising a memory for storing three dimensional images.

3. The system of claim 1 wherein the array of transducer elements operates as a sparse array.

4. The system of claim 1 wherein the second housing further comprises a control circuit to control scanning of a three dimensional volume within a patient.

5. The system of claim 1 further comprising a beam transmission circuit.

6. The system of claim 5 further comprising a third beamformer device that receives data from the second beamformer device.

7. The system of claim 1 wherein the system includes a battery within the second housing that provides power to the system.

8. The system of claim 7 wherein the system comprises an image processor in the second housing.

9. The system of claim 1 further comprising a sparse array transmission system.

10. The system of claim 1 further comprising a sparse array receiver system.

11. The system of claim 1 further comprising a matched filter.

12. The system of claim 1 further comprising a computer program stored on a processor within the processor housing, the program generating a transmission waveform that is oversampled.

13. A hand portable 3D medical ultrasound imaging system comprising:
   a two dimensional array of transducer elements in a transducer probe housing, the transducer probe housing having a programmable delay selection circuit and a first beamformer device that receives signals from a plurality of transducer subarrays such that the first beamformer device generates a coarse image data;
   a beam transmission circuit connected to the two dimensional array of transducer elements to control scanning of a three dimensional volume within a patient; and
   a second beamformer device and a subarray processor in a second display housing, the second beamformer being in communication with the probe housing, the second beamformer device receiving coarse image data from a first transducer subarray and receiving coarse image data from a second transducer subarray, the second beamformer generating fine image data to provide three dimensional image data in response to the subarray processor, the second display housing having a system controller, a data processor that performs scan conversion and Doppler processing operations and a display that displays image data, the second display housing being connected to the transducer probe housing with a cable, the system having weight of less than 15 lbs.

14. The system of claim 13 wherein the array of transducer elements operates as a sparse array.

15. The system of claim 13 further comprising the second beamformer device comprises a plurality of channels.

16. The system of claim 13 further comprising a third stage beamformer.

17. The system of claim 13 wherein the system generates at least 10 three dimensional images per second.

18. The system of claim 13 wherein the first beamformer device comprises a plurality of delay channels.

* * * * *